US008202728B2

(12) United States Patent
Coffey et al.

(10) Patent No.: US 8,202,728 B2
(45) Date of Patent: Jun. 19, 2012

(54) SUBSTRATES USEFUL FOR CELL CULTURE AND METHODS FOR MAKING AND USING SAME

(75) Inventors: Calvin T. Coffey, Watkins Glen, NY (US); Charlotte D. Milia, Corning, NY (US); Hongwei H. Rao, Horseheads, NY (US); Yichun C. Wang, Painted Post, NY (US); Christine C. Wolcott, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 1124 days.

(21) Appl. No.: 12/070,889

(22) Filed: Feb. 21, 2008

(65) Prior Publication Data
US 2008/0206831 A1 Aug. 28, 2008

Related U.S. Application Data

(60) Provisional application No. 60/902,665, filed on Feb. 22, 2007.

(51) Int. Cl.
*G01N 31/00* (2006.01)
*H01L 21/322* (2006.01)
*C30B 15/14* (2006.01)
*B01D 9/00* (2006.01)
*C09K 19/00* (2006.01)

(52) U.S. Cl. ...... 436/4; 436/5; 117/2; 117/3; 422/245.1; 430/20

(58) Field of Classification Search .................. 436/4, 5; 117/2, 3; 164/122.2; 257/49, 50, 51, 64, 257/65, 66, 67, 68, 69; 422/245.1; 430/20
See application file for complete search history.

(56) References Cited

U.S. PATENT DOCUMENTS

| | | | |
|---|---|---|---|
| 5,814,550 A | 9/1998 | Wolcott | 435/402 |
| 5,849,569 A | 12/1998 | Davies | 435/288.3 |
| 5,861,306 A | 1/1999 | Pugh et al. | 435/288.4 |
| 6,720,023 B1 | 4/2004 | Kim et al. | 427/2.27 |
| 2004/0228900 A1 | 11/2004 | Murphy et al. | 424/423 |
| 2005/0186249 A1 | 8/2005 | Riman et al. | 424/423 |
| 2006/0257377 A1 | 11/2006 | Atala et al. | 424/93.7 |

FOREIGN PATENT DOCUMENTS
WO 2006/032075 3/2006

OTHER PUBLICATIONS

The definition of "surface tension" from Wikipedia, the free encyclopedia. Printed on Oct. 12, 2011.*
R. Battaglino, D. Kim, J. Fu: B. Vaage, X.-Y. FU, and P. Stashenko. "c-myc is required for osteoclast differentiation"; J. of Bone and Mineral Res. 17 (5) 2002; pp. 763-773.
P.A. Ngankam, Ph. Lavalle, J.C. Voegel, L. Szyk, P. Schaaf, and F.J.G. Cuisiner, "Influence of polyelectrolyte multilayer films on calcium phosphate nucleation", J. Amer. Chem. Soc. 122 (2000), pp. 8998-9005.

(Continued)

*Primary Examiner* — Frank W Lu
(74) *Attorney, Agent, or Firm* — Susan S. Wilks

(57) ABSTRACT

Described herein are substrates coated with crystals having uniform crystalline morphology on the surface of the substrate. The coated substrates are useful in culturing and performing functional assays on cells such as, for example, resorption studies on bone cells. New methods for producing such coated substrates are also disclosed.

19 Claims, 13 Drawing Sheets

OTHER PUBLICATIONS

Barrere, C.A. van Blitterswijk, K. de Groot, and P. Layrolle, "Influence of ionic strength and carbonate on the Ca-P coating formation from SBF×5 solution", Biomaterials 23 (2002), pp. 1921-1930.

Yu-Fen Chou, Wen-An Chiou, Yuhuan Xu, James C.Y. Dunn, and Benjamin M. Wu, "The effect of pH on the structural evolution of accelerated biomimetic apatite", Biomaterials (2004) pp. 5323-5331.

Barrere, C.A. van Blitterswijk, K. de Groot, and P. Layrolle, "Nucleation of biomimetric Ca-P coating on Ti6Al4V from SBF×5 solution: influence of magnesium", Biomaterials 23 (2002) pp. 2111-2220.

Sergey V. Dorozhkin; "Calcium Orthophosphates"; J Mater Sci; vol. 42; pp. 1061-1095; 2007.

A. Cuneyt Tas and Sarit B. Bhaduri; "Rapid coating of Ti6Al4V at room temperature with a calcium phosphate solution simliar to 10× simulated body fluid"; J. Mater. Res.; vol. 19; pp. 2742-2749; Sep. 2004.

A. Rezania, et al., "The detachment strength and morphology of bone cells contacting materials modified with a peptide sequence found within bone sialoprotein," Adhesive Peptide and Bone Cell Adhesion, 1997, John Wiley & Sons, Inc., pp. 9-19.

A. Rezania, et al., "Biomolecular Surface Engineering of Materials for Controlling Bone Cell Adhesion and Spreading," Mat. Res. Soc. Symp. Proc., vol. 530, 1998, Materials Research Society, pp. 99-103.

A. Rezania, et al., "Integrin Subunits Responsible for Adhesion of Human Osteoblast-like Cells to Biomimetic Peptide Surfaces", Journal of Orthopaedic Research, The Journal of Bone and Joint Surgery, Inc., vol. 17, pp. 615-623, 1999.

A. Rezania, et al., "Biomimetic Peptide Surfaces That Regulate Adhesion, Spreading, Cytoskeletal Organization, and Mineralization of the matrix Deposited by Osteoblast-like Cells," Biotechnol. Prog., 1999, vol. 15, pp. 19-32.

* cited by examiner

⊢——⊣ 5 µm

⊢——⊣ 1 µm

|⎯⎯⎯⎯| 5 μm

|⎯⎯⎯⎯| 2 μm

⊢———⊣ 5 μm

⊢——⊣ 300 nm

Figure 13a
Figure 13b
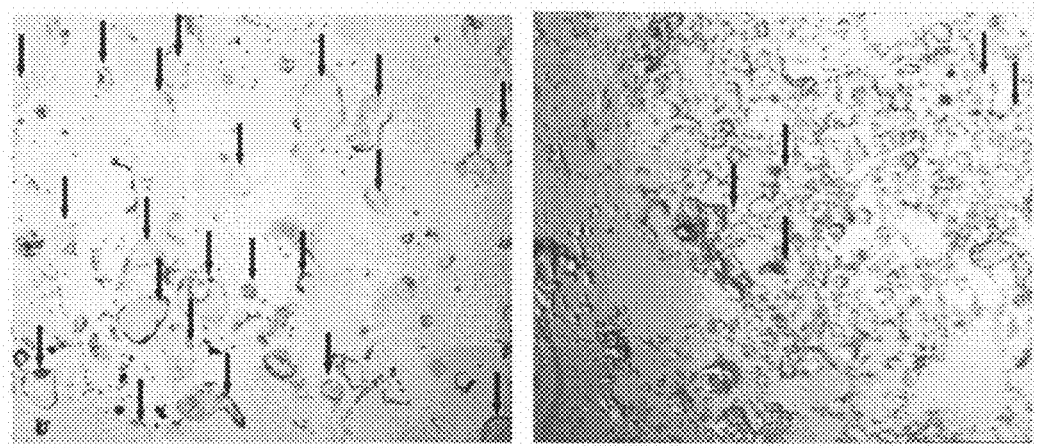
Figure 14a
Figure 14b
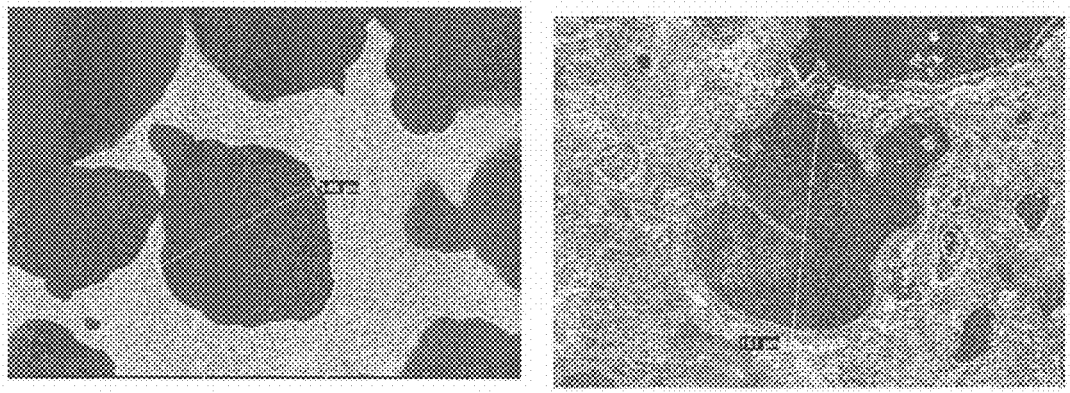

SUBSTRATES USEFUL FOR CELL CULTURE AND METHODS FOR MAKING AND USING SAME

CROSS-REFERENCE TO RELATED APPLICATIONS

This application claims the benefit of U.S. Provisional Application Ser. No. 60/902,665 filed on Feb. 22, 2007, which is incorporated by reference herein.

FIELD

This invention relates to coatings for cell culture surfaces. More particularly, this invention relates to coatings for cell culture surfaces which are derived from hydroxyapatite. The invention also relates to methods for making and using these coatings.

BACKGROUND

In vitro culturing of cells provides material necessary for cell biology research, and provides much of the basis for advances in the fields of pharmacology, physiology and toxicology. However, isolated cultured eukaryotic cells living in an incubator in a culture vessel bathed in cell culture media often have very different characteristics compared to individual cells in vivo. Information obtained from experiments conducted on primary and secondary cultures of eukaryotic cells is informative to pharmacologists, physiologists and toxicologists only to the extent that cultured cells have the same characteristics as intact cells.

Cells can grow on surfaces of cell culture vessels. For example, cells in liquid media can be introduced into a cell culture vessel such as a cell culture flask or a multi-well cell culture plate, the cell culture vessel placed into a suitable environment such as an incubator, and the cells allowed to settle onto a surface of the cell culture vessel where they attach, grow, and divide. However, some cells perform better than others when growing on particular surfaces. Some cells require different surfaces in order to maintain a more natural phenotype, and to provide optimal in vitro data.

Conditions of cell culture affect the characteristics of cells in culture, and therefore affect the value of data obtained from cells in culture. There is a need in the industry to provide cell culture surfaces and conditions to provide data that is more highly correlated with in vivo cell behavior.

SUMMARY

In accordance with the purposes of the disclosed compositions, articles, and methods, as embodied and described herein are substrates coated with crystals having uniform crystalline morphology on the surface of the substrate. The coated substrates are useful in culturing and harvesting cells such as, for example, bone cells. New methods for producing such coated substrates are also disclosed. Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying figures, which are incorporated in and constitute a part of this specification, illustrate several aspects described below.

FIG. 13 shows osteoclast cells on a HA substrate of the present invention (a) and Osteologic™ coating (b) by light microscopy after 9 days in culture.

FIG. 14 shows SEM micrographs of a HA surface of the present invention (a) and Osteologic™ surface (b) after 9 days in primary rat osteoclast culture.

DETAILED DESCRIPTION

Figure 1:
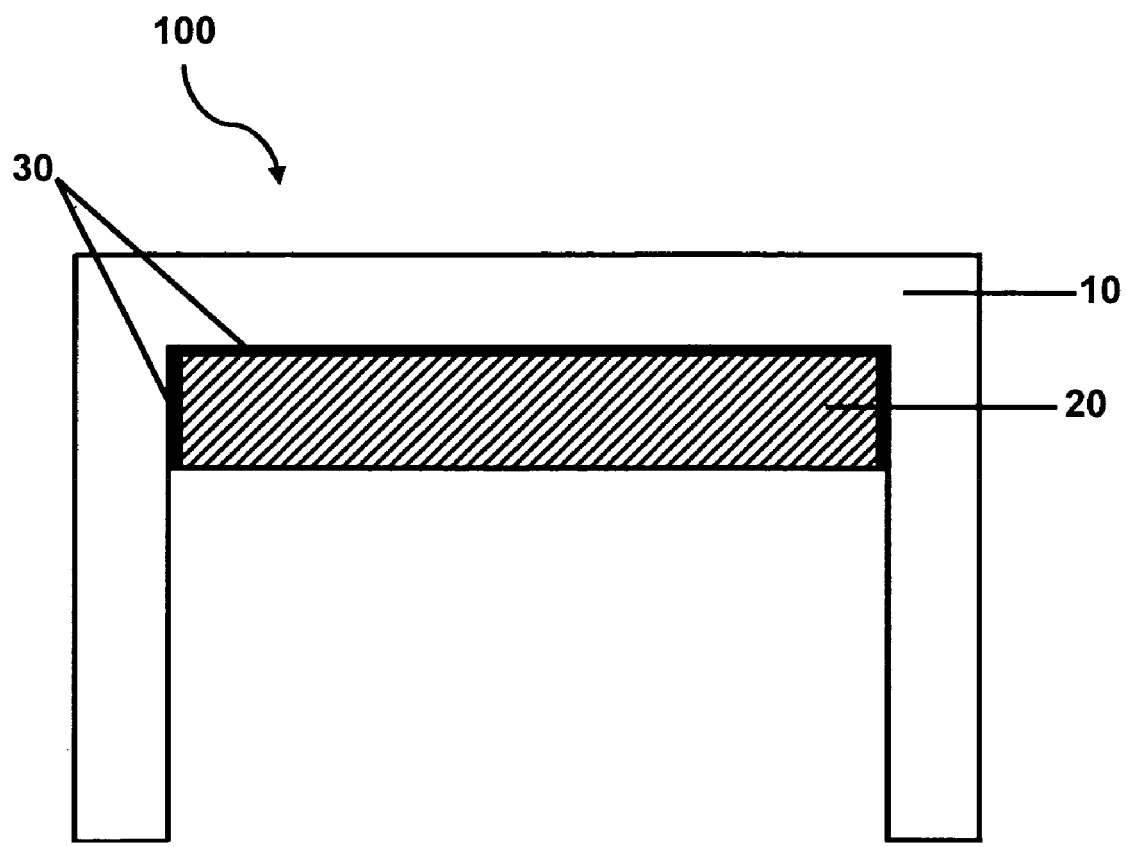
FIG. 1 shows the side-view of an inverted well of a 96 microwell plate with a solution of precursor components.

The materials, compounds, compositions, articles, devices, and methods described herein may be understood more readily by reference to the following detailed description of specific aspects of the disclosed subject matter and the Examples included therein and to the Figures.

Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

As used in the description and the appended claims, the singular forms "a," "an," and "the" include plural referents unless the context clearly dictates otherwise. Thus, for example, reference to "a composition" includes mixtures of two or more such compositions, and reference to "a precursor" includes mixtures of two or more such precursors.

"Optional" or "optionally" means that the subsequently described event or circumstance may or may not occur, and that the description includes instances where the event or circumstance occurs and instances where it does not.

Certain materials, compounds, compositions, and components disclosed herein may be obtained commercially or readily synthesized using techniques generally known to those of skill in the art. For example, the starting materials and reagents used in preparing the disclosed compounds and compositions are either available from commercial suppliers or prepared by methods known to those skilled in the art.

Reference will now be made in detail to specific aspects of the disclosed materials, compounds, compositions, articles, and methods, examples of which are illustrated in the accompanying Examples and Figures.

Culturing of adherent animal cells is generally carried out by seeding a substrate with cells in the presence of a biological medium. The cell culture substrate and medium are important in providing an environment in which cells adhere and function in a manner similar to in vivo. In the case of culturing cells, this can provide a research tool to study a number of different types of diseases and possible drugs for treating or preventing these diseases.

Hydroxyapatite ($Ca_5(PO_4)_3OH$) has been studied as an implant material due to its excellent biocompatibility and bioactivity. Hydroxyapatite can exist in a variety of different crystalline forms once it is coated on a substrate. The morphology of hydroxyapatite can be important with respect to the successful culturing and harvesting of cells, including bone cells. It is desirable that the morphology of the crystals coated on the substrate be thin, well adherent to the underlying substrate, and uniform in thickness to enable evaluation of adherent cells and to enable evaluation of changes in hydroxyapatite coating as a result of cellular function including resorption or addition of hydroxyapatite.

Therefore, there is a need for substrates that facilitate the culture of cells such as, for example, bone cells. There is a need for these substrates to possess a uniform crystalline morphology. Moreover, it may be desirable to readily control crystal morphology, (e.g., size, shape, and orientation of crystals) as needed, which can be useful in controlling cell cultures and optimizing cell response. Finally, it may be desirable to produce substrates for cell culturing using methods that can be performed in an economical manner while minimizing the possibility of contamination. Described herein are substrates and methods for producing the same that address these needs.

Described herein are coated substrates and methods of making and using them. In one aspect, a method for coating the substrate with crystals including calcium phosphate involves the following steps:
(a) contacting the substrate with a solution having a plurality of precursor components for producing the crystals, wherein the solution has a pH less than 7.0;
(b) inverting the substrate relative to the solution; and
(c) incubating the inverted substrate to produce a crystalline coating on the surface of the substrate, wherein gas generated during incubation is permitted to escape.

The term "substrate" as used herein is any article having a surface where crystals may be deposited. The substrate may assume many shapes and sizes depending upon the desired end-use of the coated substrate. In certain aspects, the substrate is capable of receiving the solution. For example, the substrate may possess one or more wells or depressions that may receive and hold the solution. An example of such a substrate may be a microwell plate having a plurality of wells with varying diameters and heights where each well can receive the solution. Alternatively, the substrate may be a flat surface such as a slide.

The substrate may be prepared from a variety of different materials. In one aspect, the substrate may be a polymer. Examples of such polymers include, but are not limited to homopolymers and copolymers of a polyester, a polyvinylchloride, a polyvinylidene fluoride, a polytetrafluoroethylene, a polycarbonate, a polyamide, a poly(meth)acrylate, a polyolefin, a polyolefin copolymer, a polystyrene, a polyethylene, polypropylene, or an ethylene/vinyl acetate copolymer. Blends of polymers are also known and may also be considered for this application. These blends may include, but not be limited to commercially available materials such as polycarbonate/ABS, PVC/ABS, polyphenyleneoxide and high impact polystyrene, but also may include novel blends of the homopolymers and copolymers listed above. These polymers may be formed into cell culture vessels including wells, multi-well plates, flasks, substrates having depressions or irregular surface structure, and the like. In addition the substrate may be a cell culture container having a virtual well formed in the substrate, such as a glass slide, or a sheet of polymer material, with a structure placed upon the substrate in a water-impermeable manner, to form sidewalls of a cell culture well.

FIG. 1 illustrates a substrate 100 in the form of a well 10. As shown in FIG. 1 the well is inverted. The substrate 100 has surfaces 30 which may be the bottom or sidewalls of a cell culture well. FIG. 1 illustrates a coating 20 on the bottom of the well 10 of the substrate 100 in an embodiment of the present invention.

In one aspect, the polymeric substrate may be modified. The polymeric substrate may be modified to change the charge of the substrate, to include active chemical moieties, to increase the amount of surface oxygen, or to change the shape or topology of the substrate. For example, the surface of the substrate may be exposed to energy such as corona discharge, plasma treatment (e.g., ammonia, nitrogen, oxygen, nitrous oxide, carbon dioxide, air, or other gases that may be activated or ionized), heat, ultraviolet radiation, gamma radiation, UV ozone, or microwave energy. An increase in surface oxygen may increase the hydrophilic nature of the substrate, which may be desirable in certain aspects. The treatment of the substrate surface may also modify the overall surface charge on the substrate, which may facilitate crystal formation. Additionally, surface treatment may vary the wettability of the surface by modifying the surface free energy and induce wetting hysteresis, which helps hold the liquid in place after inversion and during incubation. In one aspect, the substrate is polystyrene, which has been treated with plasma to increase the amount of surface oxygen.

In another aspect, the substrate is an inorganic material. Examples of inorganic materials include metals and semiconductor materials that may be surface oxidized, glass, and ceramic materials. Examples of metals that may be used as substrate materials are oxides of aluminum, chromium, titanium and steel. Semiconductor materials may be used for the substrate material and may include silicon and germanium. Glass and ceramic materials may be used for the substrate material and may include quartz, glass, porcelain, alkaline earth aluminoborosilicate glass, soda lime silicate glass and other mixed oxides. Further examples of inorganic substrate materials include zinc compounds, mica, silica and inorganic single crystal materials. It is contemplated that the substrate may include a base substrate with any of the polymeric or inorganic materials described above coated on the base substrate, thus producing a layered system. For example, a base substrate coated with silica may provide a useful support for crystal formation.

In an aspect of the present invention, the first step of the method includes contacting the substrate with a solution having a plurality of precursor components for producing the crystals. The method of contacting the substrate with the solution varies with the selection of the substrate. For example, when the substrate is a glass slide, the slide may be adhered to a gasket (e.g., flexiPerm reusable cell culture chamber manufactured by Greiner Bio One, Germany), and the solution may be added to the wells formed by the gasket adhered to the slide. In another aspect, when the substrate is a cell culture well or a microwell plate, each well is filled with a specific amount of solution. In this aspect, it is contemplated that each well is filled with the same or different solution (ie., different precursor components and/or different amounts of precursor components). The amount of solution added to each well may vary, and will depend upon the size of the well (diameter and height), the material of the substrate, and the concentration of the precursor components. In one aspect, each well is partially filled with the solution. The amount of solution that may be added to each microwell will be discussed in more detail below with respect to the inverting step. Another technique for contacting the substrate with the solution is spray coating.

A plurality of precursor components (i.e., greater than one) are used to produce the coatings described herein. Each precursor component may be any compound that can result in the formation of crystals having a morphology similar or identical to hydroxyapatite on the surface of the substrate. Each precursor component is generally a source of ions when dissolved in water or a suitable solvent. Although each precursor component is generally a salt, each precursor component may, independently, be an acid or base as well. In one aspect, each precursor component is, independently, an alkali metal halide, an alkali metal sulfate, an alkali metal carbonate, an alkali metal phosphate, an alkaline earth metal halide, an alkaline earth metal sulfate, an alkaline earth metal carbonate, or an alkaline earth metal phosphate. It is intended that carbonate also includes bicarbonate phosphate, which also includes hydrogen and dihydrogen phosphate. Likewise sulfate also includes hydrogen sulfate.

In another aspect, the precursor components include calcium chloride, magnesium chloride, sodium bicarbonate, potassium hydrogen phosphate, sodium phosphate, and sodium chloride. The ions of these components are generally present in blood plasma. Thus, solutions having these components are generally referred to as simulated body fluids or SBF. In one aspect, the solution contains the following precursor components: calcium chloride, magnesium chloride, sodium bicarbonate, potassium hydrogen phosphate, sodium phosphate, and sodium chloride. This solution is referred to herein as "synthetic SBF," which contains no buffers and the concentration of the ions present is similar to if not identical the concentrations found in blood plasma. In another aspect, the solution may include concentrations of precursor components that are greater than those in synthetic SBF. For example, the solution may be NXSBF, where N is greater than 0. In one aspect, N is greater than 0 up to 15, 2 to 10, 4 to 6, 4.5 to 5.5, or about 5. Thus, when N is 5 (i.e., 5XSBF) the solution contains five times the concentration of each ion present in synthetic SBF as defined above. The synthetic SBF solutions may be modified. For example, in certain aspects, the solution containing the precursor components does not include potassium or sulfur. In other aspects, the amount of calcium may be reduced by substituting a portion of the calcium ions with another ion such as, for example, magnesium. The concentration of each precursor component present in the solution may vary. In certain aspects, the concentration is the maximum amount of precursor component that is soluble in water alone or in combination with minor amounts of other solvents (e.g., an alcohol) or pH modifiers (e.g., acids or bases).

The initial pH of the solution as well as the pH of the solution during incubation may also vary with the concentration of the individual precursor components, the material of the substrate, the surface charge (if any) on the substrate surface, the ability of gases to escape the system, and the volume and thickness of the solution containing the precursor components. Each of these is discussed in detail below. In one aspect, the solution has an initial pH from 3 to less than 7, 4 to less than 7, 5 to less than 7, or 5.0 to 6.5. In another aspect, the initial pH of the solution is 5.0, 5.1, 5.2, 5.3, 5.4, 5.5, 5.6, 5.7, 5.8, 5.9, 6.0, 6.1, 6.2, 6.3, 6.4, or 6.5, where any value may be a lower and upper endpoint of a pH range. When using solutions containing higher concentrations of precursor components (e.g., 5XSBF), a lower pH is used in order to ensure all of the precursor components are dissolved in solution. Moreover, by varying the pH of the solution, it is possible to control the overall morphology of the crystals formed on the substrate as well as the rate of crystal formation. Additionally, as will be discussed below, the incubation time and temperature may influence crystal morphology and the rate of crystallization.

Once the substrate has been contacted with the solution or precursor components, the substrate is inverted relative to the solution. The term "inverted" is defined herein as positioning the substrate in the solution of precursor components such that the formation of particles or agglomerates on the surface is significantly reduced or prevented altogether. For example, when the substrate is a microwell or a slide adhered to a gasket, the substrate can be inverted 180°. In an embodiment, the gasket is a ring or similar structure that may be placed or adhered on top of a substrate to form a water-tight seal and create a virtual well on a substrate. In an embodiment, the gasket may form the sides of a well, or the well may be defined by the sides of a commercially available plate or multi-welled plate or other container used for cell culture. This is depicted in FIG. 1. In an embodiment, as illustrated in FIG. 1, the microwell is completely inverted. As will be discussed below, when the substrate is inverted relative to the solution, particle or agglomerate formation on the surface of the substrate is reduced or prevented. In other aspects, when the substrate is a slide, the side of the slide to be coated may be placed on top of the solution containing the precursor components. Alternatively, the slide may be vertically inserted into the solution. Both of these aspects fall under the definition of "inverted" as used herein. In the case of slides and other substrates that can be dipped into the solution, the contacting step and inverting step may be performed simultaneously.

In certain aspects, when the substrate is a container to be coated (e.g., a microwell), parameters such as well diameter, well height, well surface free energy, wetting hysteresis, and solution surface tension will determine whether or not the solution will remain in the wells upon inversion. In one aspect, the substrate may be treated with a number of surface techniques described above to change the surface charge of the substrate, which in turn may influence surface wettability. For example, when the surface of the substrate is treated to increase the amount of oxygenated groups (e.g., hydroxyl, carboxyl), the treated substrate may have a greater affinity for the solution.

Another consideration is the amount of solution used. In general, the volume of solution is sufficient to produce a suitable coating but not so great that gas generated during the process cannot diffuse from the solution. The relevance of the removal of gas will be discussed in greater detail below. The amount of solution introduced in the wells depends on the concentration of the solution and the desired thickness of the coating. In one aspect, smaller microwells such as those in 96 and 384 SBS well microplates may be filled with up to 300 μl and 100 μl of solution, respectively, and remain in the wells upon inversion.

In cases when the solution does not remain in the well upon inversion, the solution may be held in place with a gas-permeable membrane or other device that permits escape of gases generated during incubation and crystal formation. For example, in larger microwells such as those in 24, 12, or 6 well plates, the solution may not remain in the wells upon inversion and, thus, needs to be held in place. The requirement that the membrane or other device be gas-permeable will be discussed below.

The thickness and size of the membrane may vary depending upon the size of the container, the amount of solution in the container, and the amount of gas generated during incubation. The membrane is generally a hydrophobic material and does not react or dissolve when in contact with the solution. The membrane may have a flexible outside edge so that when fitted into a container there are no leaks, and further may be constructed with rigid components for support.

Suitable gas permeable, liquid impermeable membranes may be made of one or more membranes known in the art. Membranes typically are made of suitable materials that may include for example: polystyrene, polyethylene, polycarbonate, polyolefin, ethylene vinyl acetate, polypropylene, polysulfone, polytetrafluoroethylene (PTFE) or compatible fluoropolymer, a silicone rubber or copolymer, poly(styrene-butadiene-styrene) or combinations of these materials. In one aspect, the membrane is composed of Gortex. As manufacturing and compatibility for the growth of cells permits, various polymeric materials may be utilized. For its known competency, then, polystyrene may be a suitable material for the membrane (of about 0.003 inches in thickness, though various thicknesses are also permissive of cell growth). As such, the membrane may be of any thickness, for example between about 25 and 250 microns, but ideally between approximately 25 and 125 microns. In one aspect, the gas-permeable membrane may be structured and arranged to form a "plunger" when inserted into the container.

Figure 6A:
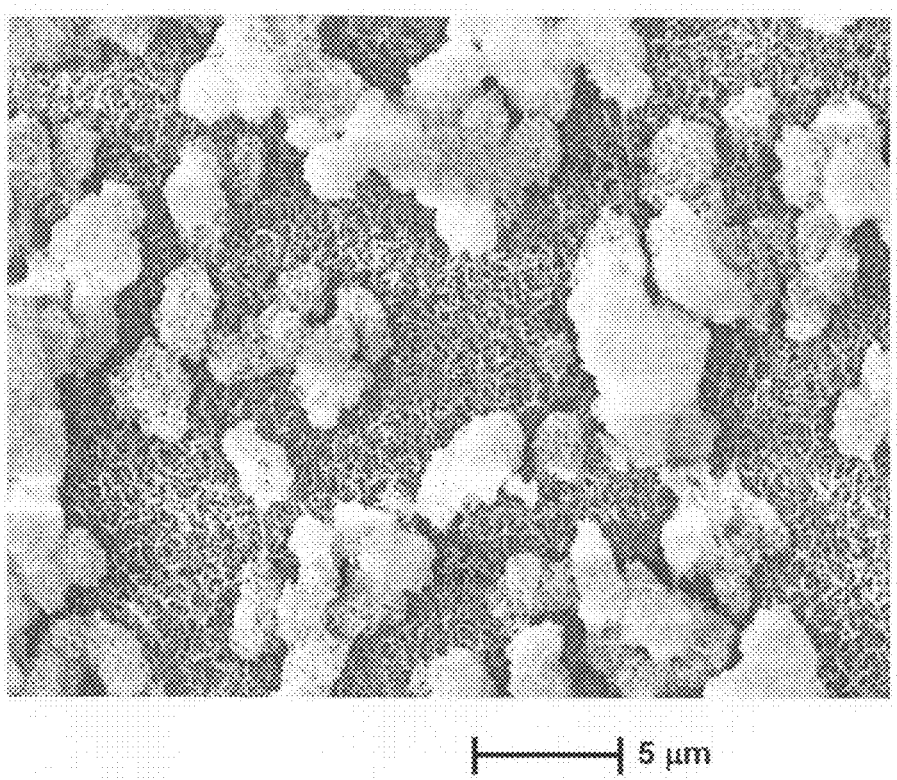
FIGS. 6a and 6b show SEM images at two different magnifications of typical sphere and lawn morphology of hydroxyapatite coatings incubated in an upright position.

After the substrate is inverted relative to the solution, the substrate is incubated to produce crystals on the surface of the substrate. Not wishing to be bound by theory, it is believed that there are two phases during incubation: an induction phase and a crystal growth phase. These phases may be monitored according to solution pH changes or kinetics. Two types of crystal nucleation reactions take place during the induction phase. Homonucleation may occur when crystals nucleate in solution, which produces a cloudy solution during incubation. At the same time, crystals may also nucleate on the substrate surface and grow epitaxially, leaving a film on the substrate surface. This is referred to as heteronucleation. With the substrate inverted relative to the solution during incubation, the surface of the substrate is coated with heterogeneously nucleated crystals only. Gravity prevents homonucleated crystals from adhering to the inverted substrate surface to produce undesirable spherical particles or agglomerates. The particles or agglomerates may be from less than a micron in diameter up to several microns. Referring to FIG. 6a, particles and/or agglomerates are on a lawn of platy crystals. The term "lawn of platy crystals" is defined herein as a homogeneous coating of crystals on the substrate surface (e.g., uniform crystal thickness and coating with no exposed surfaces on the substrate).

The temperature and duration of incubation may vary depending upon the desired morphology of the crystals coated on the substrate. The incubation temperature during generally does not require elevated temperatures such as that used in sintering. For example, it may be desirable to have a longer incubation time at a lower temperature to produce smaller crystals on the surface of the substrate. In one aspect, the incubation temperature is less than 100° C. In another aspect, the incubation step is performed at a temperature up to 90° C. for up to 72 hours. In another aspect, the incubation step is performed at a temperature from room temperature to 90° C., 30° C. to 80° C., or 40° C. to 60° C. from 1 to 72 hours, 2 to 36 hours, 2 to 24 hours, or 2 to 18 hours. The methods described herein are capable of coating the substrate quickly and effectively. This is due in part that higher concentrations of the precursor components can be used without the risk of particle or agglomerate formation (i.e., homonucleation) on the surface of the substrate.

Depending upon the selection of the precursor components, gases may be produced during incubation and crystallization. For example, if the solution of precursor components is acidic and bicarbonate is added to the solution, $CO_2$ gas is produced. Not wishing to be bound by theory, the removal of the gas may influence the pH of the solution, which in turn may influence the rate and amount of crystal formation. Depending upon the components present in the solution, crystal formation may be sensitive to changes in pH. For example, when bicarbonate is added to an acidic solution, $CO_2$ is generated. If $CO_2$ is removed from the system, the equilibrium is shifted to the right and more acid in solution is removed (i.e., reacts with bicarbonate). This results in an increase in pH. If $CO_2$ is not removed, an equilibrium is reached, and no further change in acid concentration and pH occurs (i.e., bicarbonate does not react any further with the acid). Thus, where crystal growth on the substrate is sensitive to the pH of the solution, removal of gases generated during incubation may be performed to promote crystal formation.

In certain aspects, when the substrate is an open container such as a microwell, the container is open and permits gas to be released during incubation. In this aspect, the diameter and height of the well as well as the amount of and surface tension of solution introduced into each well will determine whether or not the solution will remain in the well upon inversion of the microwell. For example, when the surface of the substrate is hydrophilic (either naturally or by surface treatment to increase the surface oxygen), the solution may adhere to the inverted container. In other situations where the solution does not remain in the container upon inversion but pours out, a gas-permeable membrane as described above may be inserted into the container to prevent leakage of the solution from the container upon inversion of the container.

In other aspects, when the substrate includes a series of substrates (e.g., a stack of microplates or Petri dishes), during incubation a slight vacuum may be applied to remove gas from the stacked system. In the alternative, the stacked system may be arranged such that the each plate or dish is loosely stacked so that any gases generated during incubation may escape.

In embodiments, after the incubation step, the substrate is coated with crystals. In embodiments, these crystals may be, for example, calcium phosphate. Subsequent steps may be performed on the coated substrate including washing the substrate with water, drying the substrate by applying a stream of air or heating the coated substrate, and sterilizing the coated substrate (e.g., exposing the substrate to gamma radiation).

The thickness of the coating on the substrate may vary depending upon the substrate to be coated as well as the nature and concentration of precursor components selected. When the method described herein is performed only once, the thickness of the coating ranges from 200 nm to 800 nm, 200 nm to 700 nm, 200 nm to 600 nm, 200 nm to 500 nm, 200 nm to 400 nm, 300 nm to 800 nm, 400 nm to 800 nm, 500 nm to 800 nm, or 600 nm to 800 nm. If thicker coatings are desired, the contacting, inverting, and incubation steps described above may be performed multiple times sequentially to produce thicker coatings. In certain aspects, thinner coatings are desirable (e.g., less than one micron) in order to better visualize the cells on the substrate and improve sensitivity to cell resorption.

In embodiments of the present invention, the substrate may be coated with crystals in a variety of patterns and designs. For example, a removable adhesive tape or mask may be placed on the surface of the substrate to produce a pattern or design of exposed substrate that ultimately will be coated with crystals. The tape or mask may then be removed after incubation and crystal formation. Alternatively, if the substrate is to be treated in order to increase surface oxygen, prior to surface treatment, a removable adhesive tape or mask may be placed on the surface of the substrate. Here, crystal formation may occur only on the portions or section of the substrate that have been surface treated, or, if crystals form on masked areas they are more easily removed during subsequent washing steps.

In embodiments of the present invention, the crystal coatings produced herein are calcium phosphate crystals. In one aspect, the crystals may be hydroxyapatite, which has the formula $Ca_5(PO_4)_3OH$. In another aspect, the crystals may be substituted hydroxyapatite. Substituted hydroxyapatite is hydroxyapatite with one or more atoms substituted with another atom. Substituted hydroxyapatite is depicted by the formula $M_5X_3Y$, where M is Ca, Mg, Na; X is $PO_4$ or $CO_3$; and Y is OH, F, Cl, or $CO_3$. Minor impurities in the hydroxyapatite structure may also be present, and may include the following ions: Zn, Sr, Al, Pb, or Ba. In another aspect, the calcium phosphate may be a calcium orthophosphate. Examples of calcium orthophosphates include, but are not limited to, monocalcium phosphate anhydrate, monocalcium phosphate monohydrate, dicalcium phosphate dihydrate, dicalcium phosphate anhydrous, octacalcium phosphate, beta tricalcium phosphate, alpha tricalcium phosphate, super alpha tricalcium phosphate, or tetracalcium phosphate. In certain aspects, the calcium phosphate crystals include crystals possessing carbonate groups ($CO_3$), which may facilitate adhesion of certain types of cells such as, for example, bone cells, during culturing. In other aspects, the calcium phosphate crystals may also include calcium-deficient hydroxyapatite, which may preferentially adsorb proteins useful in cell culturing such as bone matrix proteins.

Embodiments of crystal coatings produced herein generally have a high surface area and pore volume due to their plate-like or reticular crystallite morphology. High surface area and porosity may increase the rate of cell resorption, which may ultimately increase the sensitivity of the cell resorption assay. In embodiments of the present invention, the coatings produced herein may have minimal to no spherical particles on the coating surface. As discussed above, inverting the substrate relative to the solution prevents particles or agglomerates that nucleate in solution from collecting or growing on the coated substrate, which is prevented by gravity. Thus, crystal growth occurs uniformly and evenly on the surface of the substrate in the absence or substantial absence of particles or agglomerates, which is desirable for cell culturing. Moreover, when the crystals are grown having a uniform thickness, which enables better evaluation of adherent cells and changes in the crystal coating. Additionally, the presence of particles or agglomerates produces opaque coatings, which also reduces the ability to evaluate cells by microscopy. The lack of particles or agglomerates also ensures better adhesion of the crystals to the surface of the substrate. Finally, the coated substrates are more resistant to delamination of the crystalline layer by solutions such as cell culture medium.

The coated substrates produced herein may be used to culture cells. In one aspect, the method involves (a) depositing a parent set of cells on any of the coated substrates produced herein, and (b) culturing the substrate with the deposited cells. By modifying the composition and morphology of the crystals on the substrate surface, it may be possible to facilitate cellular response to the coating. For example, if magnesium is present in the crystal coating (i.e., substituted hydroxyapatite), the magnesium may directly stimulate osteoblast proliferation.

Many types of cells may be cultured on embodiments of the substrate of the present invention including, but not limited to, stem cells, committed stem cells, differentiated cells, and tumor cells. Examples of stem cells include, but are not limited to, embryonic stem cells, bone marrow stem cells and umbilical cord stem cells. Other examples of cells used in various embodiments include, but are not limited to, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, and neurons.

In one aspect, bone cells (e.g., osteoclasts, osteocytes, and osteoblasts) and bone cell precursors (e.g., monocytes and macrophages) may be cultured with the coated substrates produced herein. For example, referring to FIG. 13a, individual osteoclasts (indicated by the black arrows) are clearly visible on a surface produced by the present invention (see example 10). The better resolution of the cells in FIG. 13a makes cell counting easier, which is an important feature. FIG. 14a is an SEM micrograph of the same coating. Referring to FIG. 14a, a number of resorption pits (i.e., the dark images) were present. Resorption pits are formed when osteoclasts release hydrogen ions that may dissolve the crystalline material. Upon dissolution, the cell forms a pit or indentation in the crystalline layer. The ability to effectively quantify the resorption pits (e.g., pit area, number of pits, etc.) is one way to evaluate the ability of cells to adhere and resorb to the coated substrate. Referring to FIG. 14a, the resorption pits are well-defined by SEM or optical microscopy. Thus, not only are the coated substrates described herein useful in cell adhesion and growth, they also facilitate the evaluation of the cells. Moreover, when the coated surfaces are well plates, the plates comply with the requirements of the Society of Biomolecular Sciences (SBS).

Cells useful herein may be cultured in vitro, derived from a natural source, genetically engineered, or produced by any other means. Any natural source of prokaryotic or eukaryotic cells may be used.

A typical or abnormal cells such as tumor cells may also be used herein. Tumor cells cultured on substrates described herein may provide more accurate representations of the native tumor environment in the body for the assessment of drug treatments. Growth of tumor cells on the substrates described herein may facilitate characterization of biochemical pathways and activities of the tumor, including gene expression, receptor expression, and polypeptide production, in an in vivo-like environment allowing for the development of drugs that specifically target the tumor.

Cells that have been genetically engineered may also be used herein. The engineering involves programming the cell to express one or more genes, repressing the expression of one or more genes, or both. Genetic engineering may involve, for example, adding or removing genetic material to or from a cell, altering existing genetic material, or both. Embodiments in which cells are transfected or otherwise engineered to express a gene may use transiently or permanently transfected genes, or both. Gene sequences may be full or partial length, cloned or naturally occurring.

In another aspect, described herein is method for growing cells or tissue, which includes (a) depositing a parent set of cells that are a precursor to the tissue on a substrate described herein, and (b) culturing the substrate with the deposited cells to promote the growth of the cells and ultimately the tissue. It is also contemplated that viable cells may be deposited on the coated substrates produced herein and cultured under conditions that promote tissue growth. Tissue grown (i.e., engineering) from any of the cells described above is contemplated with the coated substrates produced herein. The coated substrates may support many different kinds of precursor cells, and the substrates may guide the development of new tissue. The production of tissues has many applications including wound healing. It is contemplated that tissue growth may be performed in vivo or ex vivo.

In certain instances, it is desirable to remove cells or tissue from the coated substrate. Techniques known in the art for removing cells include, but are not limited to, mechanical scraping, sonication, chemical/enzymatic treatment, or a combination thereof. Other techniques involve adjusting the pH or temperature or the addition of ions to release attached cells. In one aspect, when the coating is calcium phosphate, cells may be removed by dissolution of the coating by lowering the pH of surrounding media.

In embodiments, the coated substrates produced herein may comprise one or more bioactive molecules that may facilitate cell adhesion to the crystal coating, promote cell function, or promote cell growth. In one aspect, one or more bioactive molecules may be part of the composition used to produce the crystal coating. In this aspect, the bioactive molecule may be dispersed uniformly throughout the crystal coating. This coated substrate may also be referred to as a bioceramic or BIOCER. In another aspect, once the crystal coating has been produced, the coating is contacted with one or bioactive molecules.

Bioactive molecules include human or veterinary therapeutics, nutraceuticals, vitamins, salts, electrolytes, amino acids, peptides, polypeptides, proteins, carbohydrates, lipids, polysaccharides, nucleic acids, nucleotides, polynucleotides, glycoproteins, lipoproteins, glycolipids, glycosaminoglycans, proteoglycans, growth factors, differentiation factors, hormones, neurotransmitters, pheromones, chalones, prostaglandins, immunoglobulins, monokines and other cytokines, humectants, minerals, electrically and magnetically reactive materials, light sensitive materials, anti-oxidants, molecules that may be metabolized as a source of cellular energy, antigens, and any molecules that may cause a cellular or physiological response. Any combination of molecules may be used, as well as agonists or antagonists of these molecules. Glycoaminoglycans include glycoproteins, proteoglycans, and hyaluronan. Polysaccharides include cellulose, starch, alginic acid, chytosan, or hyaluronan. Cytokines include, but are not limited to, cardiotrophin, stromal cell derived factor, macrophage derived chemokine (MDC), melanoma growth stimulatory activity (MGSA), macrophage inflammatory proteins 1 alpha (MIP-1 alpha), 2, 3 alpha, 3 beta, 4 and 5, interleukin (IL) 1, IL-2, IL-3, IL-4, IL-5, IL-6, IL-7, IL-8, IL-9, IL-10, IL-11, IL-12, IL-13, TNF-alpha, and TNF-beta. Immunoglobulins useful herein include, but are not limited to, IgG, IgA, IgM, IgD, IgE, and mixtures thereof. Amino acids, peptides, polypeptides, and proteins may include any type of such molecules of any size and complexity as well as combinations of such molecules. Examples include, but are not limited to, structural proteins, enzymes, and peptide hormones.

The term bioactive molecule also includes fibrous proteins, adhesion proteins, adhesive compounds, deadhesive compounds, and targeting compounds. Fibrous proteins include collagen and elastin. Adhesion/deadhesion compounds include fibronectin, laminin, thrombospondin and tenascin C. Adhesive proteins include actin, fibrin, fibrinogen, fibronectin, vitronectin, laminin, cadherins, selectins, intracellular adhesion molecules 1, 2, and 3, and cell-matrix adhesion receptors including but not limited to integrins such as $\alpha_5\beta_1$, $\alpha_6\beta_1$, $\alpha_7\beta_1$, $\alpha_4\beta_2$, $\alpha_2\beta_3$, and $\alpha_6\beta_4$.

The term bioactive molecule also includes leptin, leukemia inhibitory factor (LIF), RGD peptide, tumor necrosis factor alpha and beta, endostatin, angiostatin, thrombospondin, osteogenic protein-1, bone morphogenic proteins 2 and 7, osteonectin, somatomedin-like peptide, osteocalcin, interferon alpha, interferon alpha A, interferon beta, interferon gamma, interferon 1 alpha, and interleukins 2, 3, 4, 5 6, 7, 8, 9, 10, 11, 12, 13, 15, 16, 17 and 18.

The term "growth factor" as used herein means a bioactive molecule that promotes the proliferation of a cell or tissue. Growth factors useful herein include, but are not limited to, transforming growth factor-alpha. (TGF-alpha), transforming growth factor-beta. (TGF-beta), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5 s, NGF 7.0 s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor (HGF), glial neurotrophic growth factor (GDNF), stem cell factor (SCF), keratinocyte growth factor (KGF), transforming growth factors (TGF), including TGFs alpha, beta, beta1, beta2, and beta3, skeletal growth factor, bone matrix derived growth factors, and bone derived growth factors and mixtures thereof. Some growth factors may also promote differentiation of a cell or tissue. TGF, for example, may promote growth and/or differentiation of a cell or tissue. Some preferred growth factors include VEGF, NGFs, PDGF-AA, PDGF-BB, PDGF-AB, FGFb, FGFa, HGF, and BGF.

The term "differentiation factor" as used herein means a bioactive molecule that promotes the differentiation of cells or tissues. The term includes, but is not limited to, neurotrophin, colony stimulating factor (CSF), or transforming growth factor. CSF includes granulocyte-CSF, macrophage-CSF, granulocyte-macrophage-CSF, erythropoietin, and IL-3. Some differentiation factors may also promote the growth of a cell or tissue. TGF and IL-3, for example, may promote differentiation and/or growth of cells.

The term "adhesive compound" as used herein means a bioactive molecule that promotes attachment of a cell or tissue to a fiber surface. Examples of adhesive compounds include, but are not limited to, fibronectin, vitronectin, and laminin.

The term "deadhesive compound" as used herein means a bioactive molecule that promotes the detachment of a cell or tissue from a fiber. Examples of deadhesive compounds include, but are not limited to, thrombospondin and tenascin C.

The term "targeting compound" as used herein means a bioactive molecule that functions as a signaling molecule inducing recruitment and/or attachment of cells or tissues to a fiber. Examples of targeting compounds and their cognate receptors include attachment peptides including RGD peptide derived from fibronectin and integrins, growth factors including EGF and EGF receptor, and hormones including insulin and insulin receptor.

In another aspect, described herein are methods for determining an interaction between a known cell line and a drug, which includes (a) depositing the known cell line on a coated substrate described herein; (b) contacting the deposited cells with the drug; and (c) identifying a response produced by the deposited cells upon contact with the drug.

With a known cell line immobilized on embodiments of the coated substrates of the present invention, it is possible to screen the activity of drugs when the drug interacts with the immobilized cells. Depending upon the cells and drugs to be tested, the cell-drug interaction may be detected and measured using a variety of techniques. For example, the cell may metabolize the drug to produce metabolites that may be readily detected in culture media. Alternatively, the drug may induce the cells to produce proteins or other biomolecules. The proteins or other biomolecules may then be detected in culture media. The substrates described herein provide an environment for the cells to more closely mimic the in vivo nature of the cells in an ex vivo environment. The substrates may be used in high throughput applications for analyzing drug/cell interactions. High throughput applications utilize multiwell tissue culture chambers with densities up to about 1536 wells per plate. Thus, increasing the population of cells per well would serve to increase the measured signals.

EXAMPLES

The following examples are set forth below to illustrate methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that may be used to optimize the product purity and yield obtained from the described process. Only reasonable and routine experimentation will be required to optimize such process conditions.

Example 1

Preparation of Coated Substrates

The following steps were used to prepare the coated substrates:

A. Preparation of Mineral Solutions Containing Precursor Components

The mineral solutions containing the precursor components are provided in Table 1. Table 2 provides concentrations of each ion present in the mineral solutions. For comparison, ion concentrations of blood plasma are provided in Table 2. The synthetic SBF in Table 2 as well as the other mineral solutions in Table 2 with the exception of blood plasma contains no buffers (e.g., tris/HCl or Hepes). In certain experiments described below, the magnesium and carbonate were intentionally included for modification of the hydroxyapatite stoichiometry. In addition, sodium bicarbonate serves as an inorganic pH modifier for control of mineralization solution chemistry. Sodium chloride is present in mineralization solutions at a much higher level than the other salts, and determines the overall ionic strength of solution, which may affect pH kinetics.

In the case of the synthetic mineral solutions SBF5X- and SBF5X-1/2SB, the solutions were prepared by adding the salts in the order listed in Table 1 ($CaCl_2$, $MgCl$, $NaHCO_3$, $K_2HPO_4$, then $Na_2SO_4$) to deionized water. The pH of the solution was titrated to a pH of approximately 4.0 to ensure all of the salts were dissolved in solution. Next, NaCl was added followed by titration with sodium hydroxide in an amount to produce a pH of 5.2-5.8.

In the case of SBF5XNaP, the order of the addition of the salts to deionized water was as follows: NaCl, $CaCl_2$, $MgCl$, $NaHPO_4$, then $NaHCO_3$. The preparation of SBF5XNaP required no pH adjustment prior to use.

In the following experiments, synthetic SBF and SBF5X were not tested, but the composition of these solutions was provided for comparison with SBF5X-, SBF5X-1/2SB, and SBF5XNaP.

TABLE 1

Precursor components and amounts used to prepare the mineral solutions

| Salt | SBF5X g/500 ml | SBF5X- g/500 ml | SBF5X- 1/2SB cg/500 ml | SBF5XNaP g/500 ml |
|---|---|---|---|---|
| $CaCl_2 2H_2O$ | 0.92 | 0.92 | 0.92 | 0.92 |
| $MgCl\ 6H_2O$ | 0.76 | 0.76 | 0.76 | 0.76 |
| $NaHCO_3$ | 0.88 | 0.88 | 0.44 | 0.42 |
| $K_2HPO_4$ | 0.43 | 0.43 | 0.43 | 0 |
| $Na_2SO_4\ 10H_2O$ | 0.40 | 0 | 0 | 0 |
| KCl | 0.56 | 0 | 0 | 0 |
| NaCl | 19.99 | 19.99 | 19.99 | 19.9 |
| $NaHPO4H2O$ | 0 | 0 | 0 | 0.55 |

TABLE 2

Concentrations (mM) of ionic components in the synthetic mineral solutions compared with blood plasma

|  | Na+ | K+ | Ca2+ | Mg2+ | Cl− | HCO3− | HPO4$^{2-}$ | SO4$^{2-}$ | Ca/P |
|---|---|---|---|---|---|---|---|---|---|
| Blood Plasma | 142 | 5 | 2.5 | 1.5 | 103 | 27 | 1 | 0.5 | 2.5 |
| Synthetic SBF | 142 | 5 | 2.5 | 1.5 | 148 | 4.2 | 1 | 0.5 | 2.5 |
| SBF(5X) | 710 | 25 | 12.5 | 7.5 | 740 | 21 | 5 | 2.5 | 2.5 |
| SBF5X- | 714 | 7.5 | 12.5 | 7.5 | 714 | 21 | 4 | 0 | 3.1 |
| SBF5X-1/2SB | 692 | 7.5 | 12.5 | 7.5 | 714 | 11 | 4 | 0 | 3.1 |
| SBF5XNaP | 699 | 0 | 12.5 | 7.5 | 714 | 10 | 8 | 0 | 1.6 |

B. Incubation

After the substrate was contacted with the appropriate mineral solution (SBF5X-, SBF5X-1/2SB, and SBF5XNaP), the substrate was incubated at either 18 hrs at 40° C. (18/40) or 4 hrs at 60° C. (4/60).

C. Washing

After incubation, the substrates were washed by soaking the substrate in a bath of deionized water, spraying deionized water on the substrate, or a combination of the two methods. Alternately, an automatic plate washer may be used to remove uncrystallized salts.

D. Drying

Drying was performed by forced hot air such as from a hair dryer. This method resulted in a reduction in drying defects like drying front rings and debris compared with drying in an oven. After drying with forced hot air, the substrate is placed in a oven for one hour at 50° C.

E. Sterilization

The dried substrates were exposed to gamma radiation. Gamma sterilization was performed at Steris Isomedix (Chester, N.Y.), at a 10-18 K Gray dosage.

Example 2

Harvesting Coated Substrates for X-Ray Diffraction

The coatings were characterized in a number of ways, which are summarized below. Crystalline phases were identified by powder X-ray diffraction (XRD), performed on material scraped from Petri dishes, incubated with equivalent solutions, times and temperatures as microplates. The coated dishes were washed, and wet coatings from several 100 mm Petri dishes were scraped and pooled for each powder XRD measurement. Coatings on the plates were assumed to be equivalent to dishes processed under the same conditions.

Example 3

Orientation and Surface Properties

When wells are filled and inverted with aqueous salt solution, the liquid remains at the bottom of the well due to surface tension (FIG. 1). In certain experiments, Corning® 96 well clear flat bottom TC-treated microplates (product #3585) were used. These plates are composed of polystyrene and have been corona treated and sterilized by gamma irradiation. These plates are referred to herein as "TCT PS." In other experiments, polystyrene plates exposed to corona treatment but not sterilized by gamma radiation were used. These plates are referred to herein as "CNG." The minimum volume (100μl) for achieving a homogenous coating is used per well. Wells may also be filled with 300 μl of solution and good coatings result.

Example 4

Figure 3A:
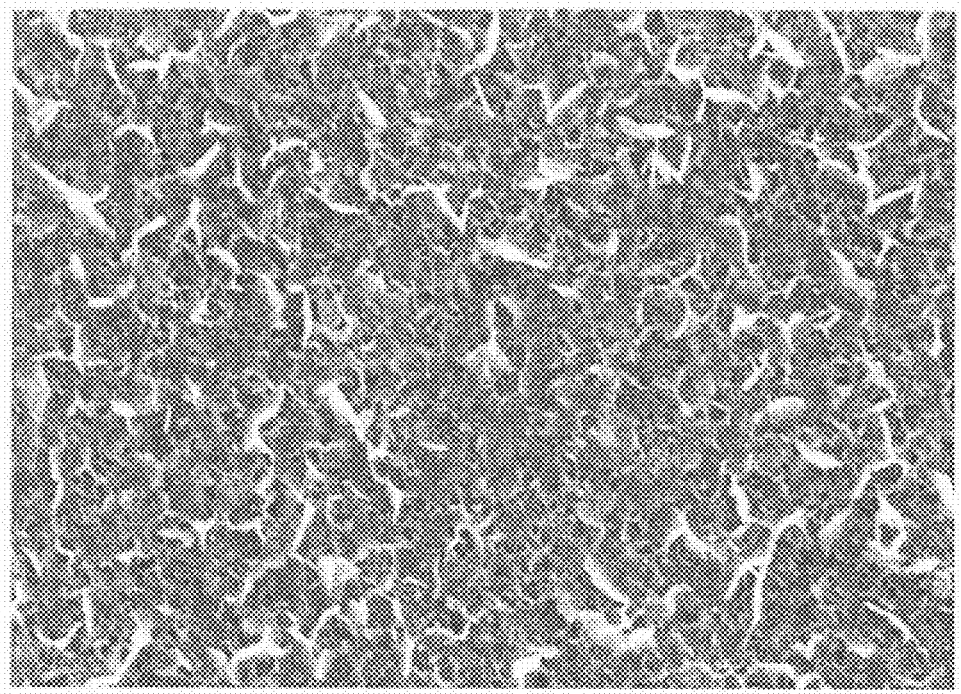
FIGS. 3a and 3b show SEM micrographs at two different magnifications of surface coatings produced by the methods of the present invention.
Figure 3B:
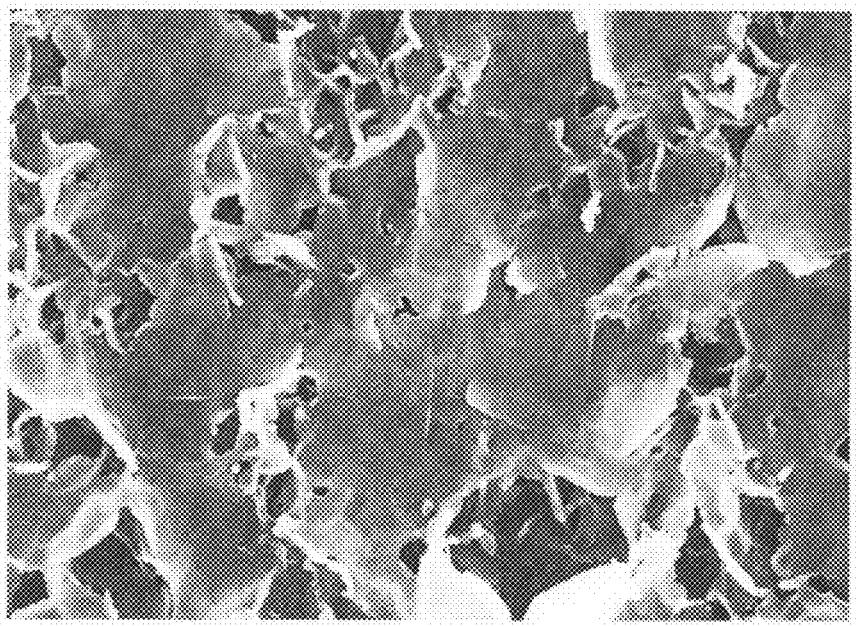
Figure 4A:
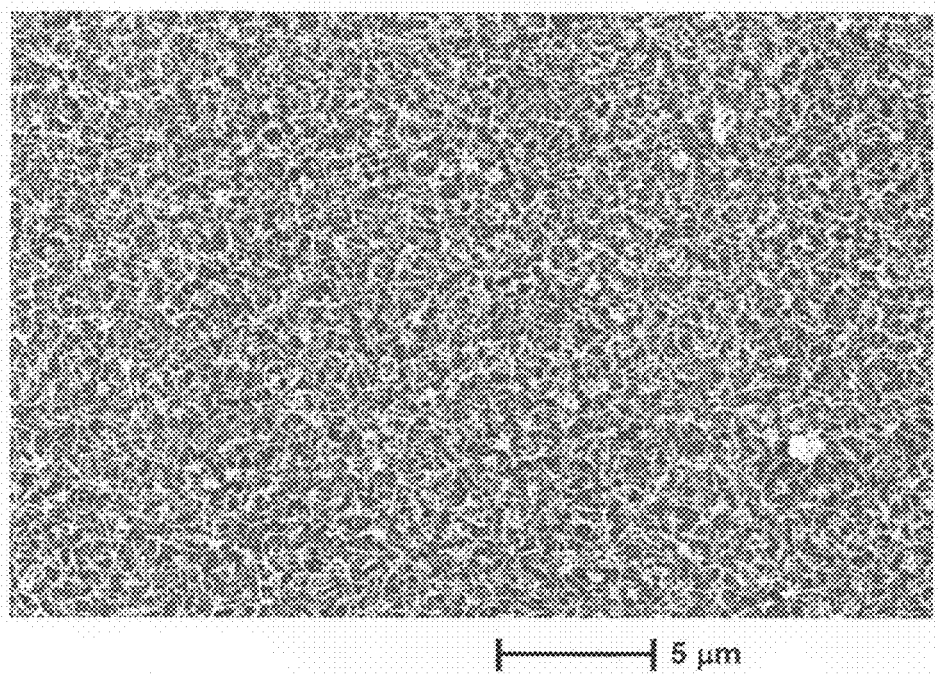
FIGS. 4a and 4b show SEM micrographs at two different magnifications of surface coatings produced by the methods of the present invention.
Figure 4B:
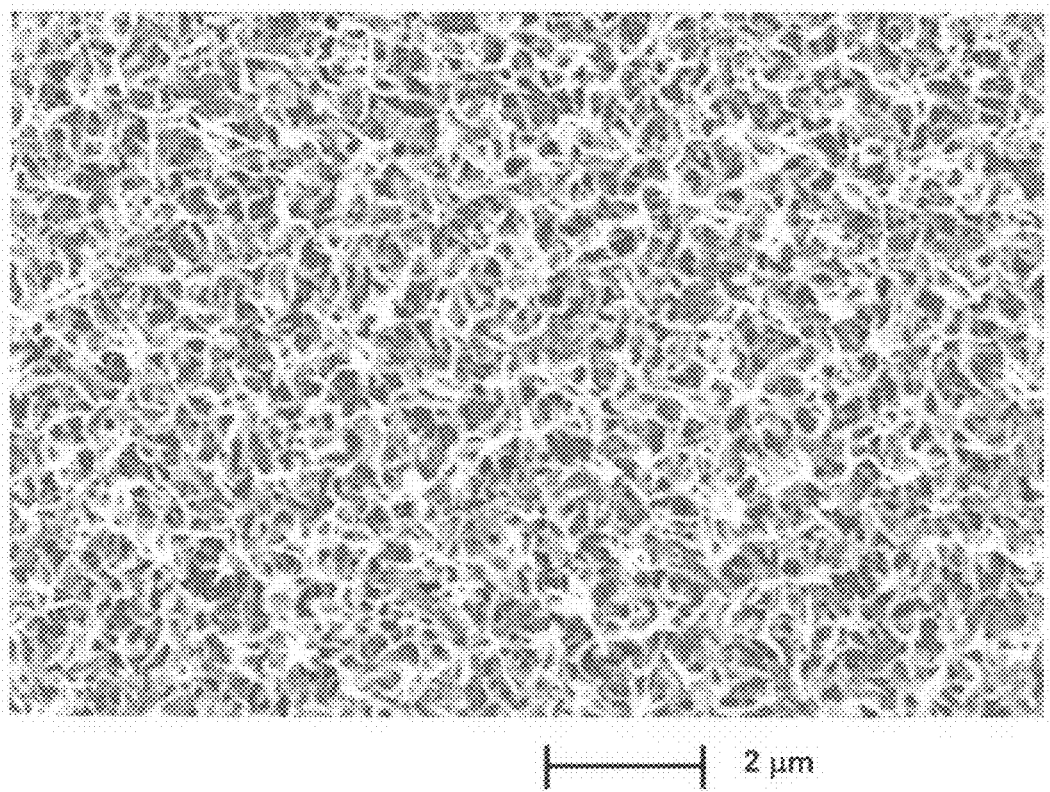

Crystal Coating Morphology Variations in Plates Incubated in Inverted Horizontal Orientation A. SBF5X- in 96 well TCT PS plates SEM images showed that slower, cooler incubation of SBF5X- (18 hrs/40° C.) resulted in a coating with flat platy morphology with plates both parallel and perpendicular to the substrate (FIGS. 3a and 3b). Faster, warmer incubation (4 hrs/60 ° C.) resulted in a more reticular morphology (FIGS. 4a and 4b). Both coatings have crystallites and spaces between crystallites on the order of hundreds of nanometers long. Thus, by modifying the incubation time and temperature, it is possible to produce different crystalline morphologies on the surface of the substrate. This may be desirable for the adherence and resorption of different types of cells on the substrate.

B. SBF5X-1/2SB in 96 well TCT PS plates

Figure 5A:
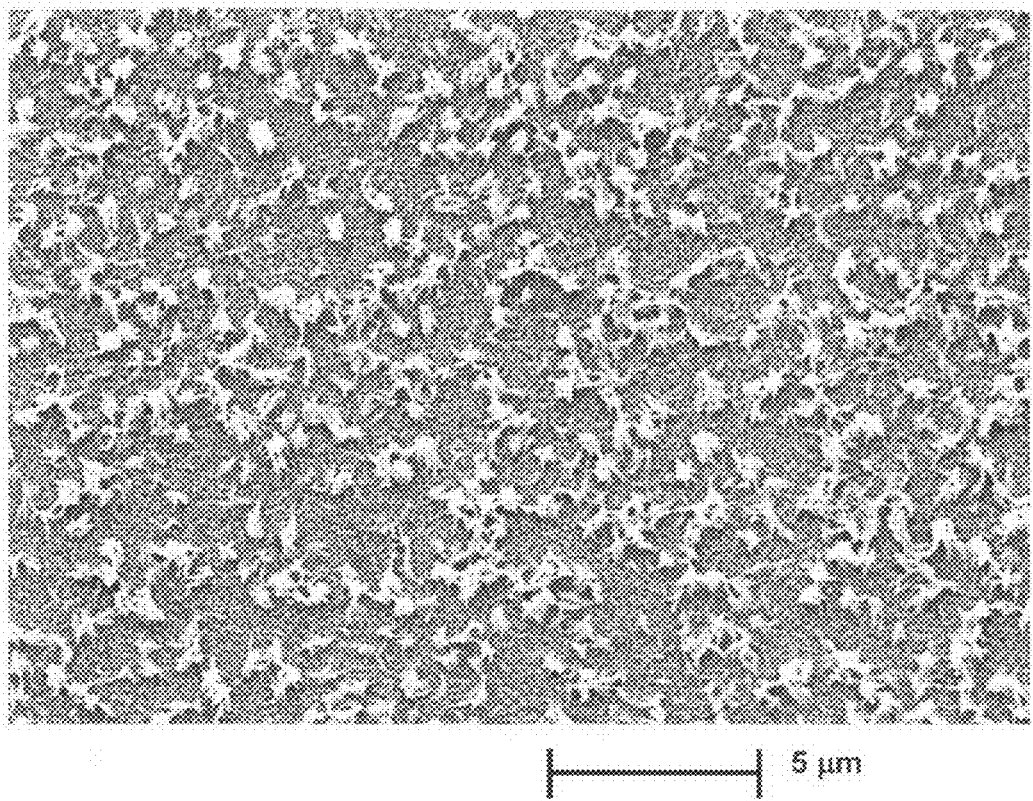
FIGS. 5a and 5b show SEM micrographs of surface coatings produced by the methods of the present invention.

Changes in mineralization solution chemistry affect the uniformity of coating formed. Reduction in sodium carbonate in plates incubated at 60° C. for 6 hours resulted in a thinner, less homogeneous coating (i.e., no lawn of crystals) (FIG. 5a).

C. $CO_2$ bubbled SBF5X- in TCT PS plates

Figure 5B:
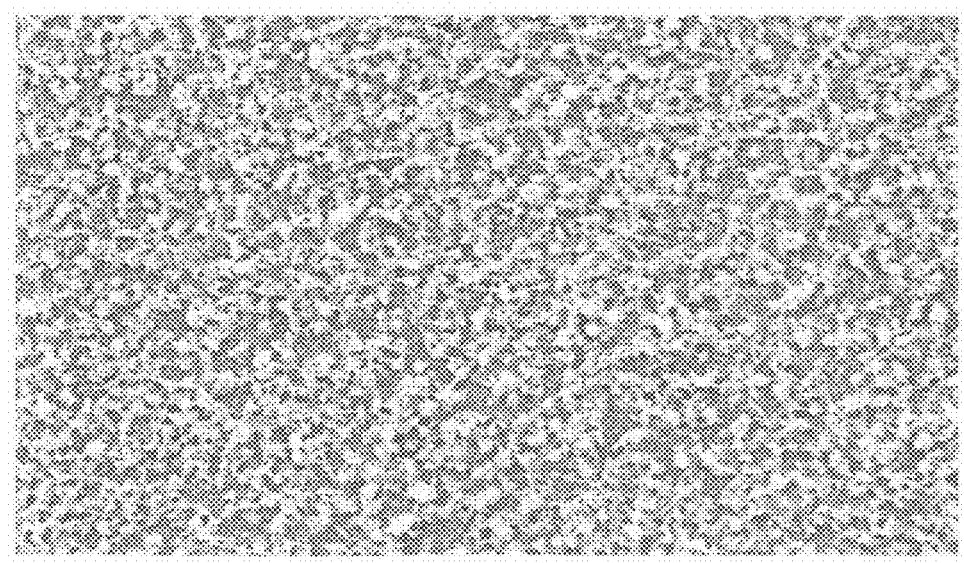

Bubbling SBF5X- with $CO_2$ gas just before incubation (6 hrs/60° C.) had a similar effect on coating morphology as Example B (FIG. 5b), resulting less homogeneous crystals. The increase in $CO_2$ also resulted in bubble-shaped defects in the coating (not shown).

D. SBF5XNaP in CNG 96 well plates

CNG plates (86 in total) were incubated with SBF5XNaP solution at various times and temperatures ranging from 4-18 hrs, and 35-60° C. SEM images recorded three different surface morphologies: amorphous coatings (0% crystalline), hydroxyapatite (HA), and hydroxyapatite tricalcium phosphate (HA+TCP) (Table 3). The preferred processing conditions for this solution were 18 hrs at 35° C., where 100% of wells observed were crystalline and only single phase hydroxyapatite (HA) was produced. It was also noted during harvesting of crystals from dishes for XRD that the crystals formed at 35° C. were better adhered to polystyrene than at other temperatures. Unlike single phase HA, HA+TCP is two phases. Coatings composed of HA+TCP are not as durable as that of HA (e.g., HA+TCP is more soluble in acidic conditions). Additionally, there is no tricalcium phosphate in bone mineral; therefore, HA+TCP may not mimic bone and ultimately support cell adhesion, differentiation, and resorption.

TABLE 3

SEM data from plates and XRD data from dishes

| Time/Temp | % Crystalline | % Reticular | % Plate-like | Phase ID |
|---|---|---|---|---|
| 4 hrs/35 C. | 0 | 0 | 0 | Amorphous |
| 11 hrs/35 C. | 17 | 17 | 0 | HA |
| 18 hrs/35 C. | 100 | 0 | 100 | HA |
| 4 hrs/47 C. | 33 | 25 | 8 | HA |
| 11 hrs/47 C. | 100 | 100 | 0 | HA + TCP |
| 18 hrs/47 C. | 100 | 100 | 0 | HA + TCP |
| 4 hrs/60 C. | 100 | 94 | 0 | HA + TCP |
| 11 hrs/60 C. | 100 | 89 | 0 | HA + TCP |
| 18 hrs/60 C. | 100 | 31 | 0 | HA + TCP |

In order to evaluate the affect of pH on crystal growth formation, CNG plates were incubated with SBF5XNaP as described above in buffered solutions (Table 4). The SBF5XNaP solutions were buffered with sodium bicarbonate and tris-hydroxylmethyl aminomethane) (TRIS). Referring to Table 4, BSBF-1 had a pH of 6.90 and BSBF-2 had a pH of 9.00. In each well of the plate, 100 μl of each solution was added. The plates were inverted and incubated for 16 hours at 35° C. After incubation, the plates were washed and dried as outlined above.

Figure 15A:
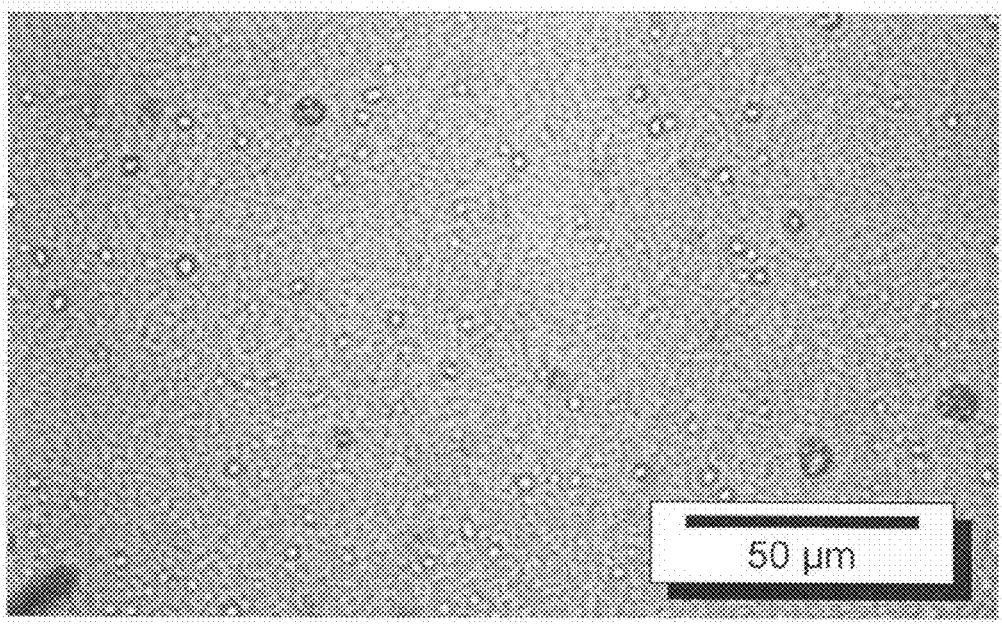
FIGS. 15a and 15b shows the surfaces of CNG plates by optical microscopy incubated with buffered solutions of SBF5XNaP.
Figure 15B:
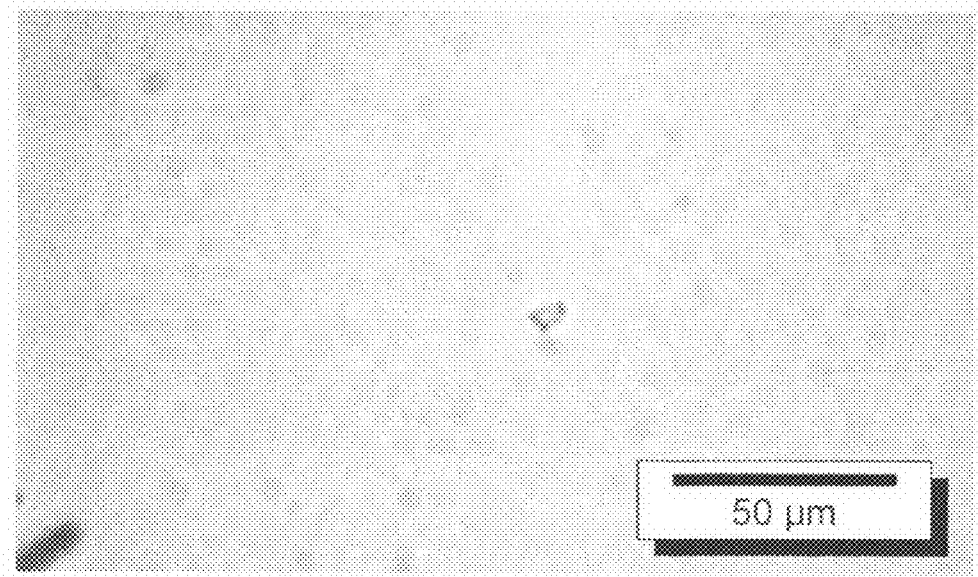

FIG. 15a shows the surface of the plate by optical microscopy (500 X) that was incubated with BSBF-1 (pH of 6.90). The coating on the surface of the plate exhibited a wormy textured layer with spherical particles on the surface of the coating. FIG. 15b shows the surface of the plate by optical microscopy (500 X) that was incubated with BSBF-2 (pH of 9.00). No crystals were present on the surface of the plate. The results indicate that buffered mineral solutions with an increased pH can affect the amount and types of crystals that are formed on the surface of the plate.

TABLE 4

| Solution | SBF5XNaP | Sodium bicarbonate | Tris | pH before incubation | pH after incubation |
|---|---|---|---|---|---|
| BSBF-1 | 200 mL | 0.168 g | 0.122 g (0.005M) | 6.90 | 6.37 |
| BSBF-2 | 200 mL | 0.168 g | 1.22 g (0.05M) | 9.00 | 8.84 |

Example 5

Coating Morphology in Dishes Incubated in Non-inverted Orientation

Figure 6B:
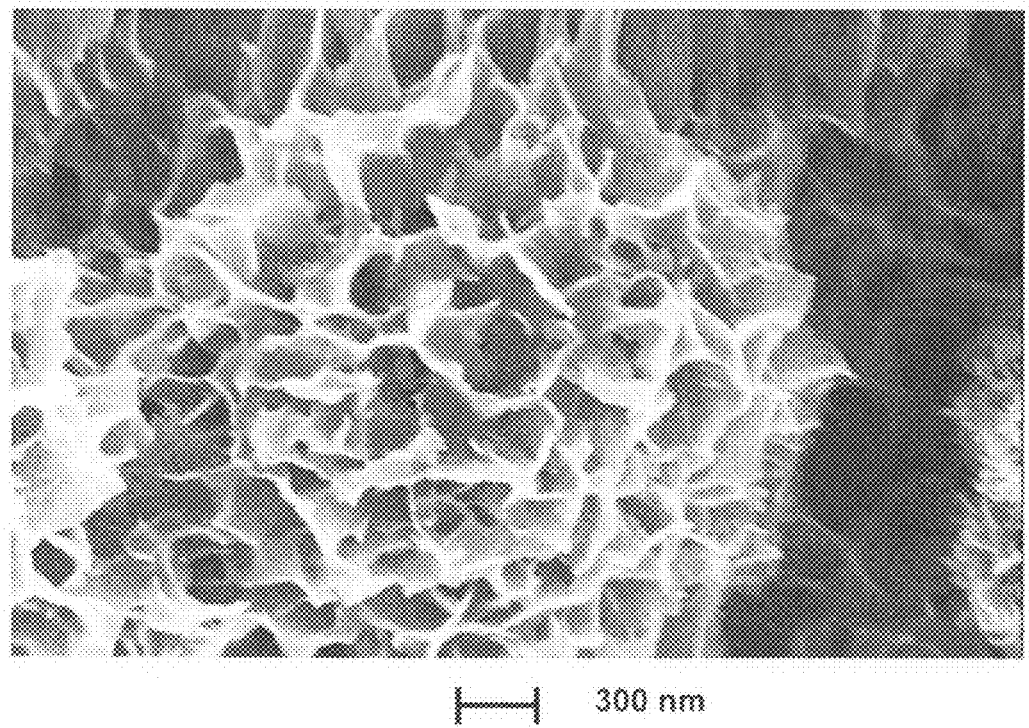

The Petri dishes used in this experiment were Corning® 60 mm TC-treated culture dishes (product #430166). These dishes are composed of polystyrene. Processing of the Petri dishes in a horizontal position without inversion resulted in coatings that were several microns in thickness and covered with a 3D "lawn and sphere" morphology (FIG. 6a). The underlying surface appeared to be coated with a lawn of platy crystals like the inverted microplates but with overlying spheres or agglomerates of about 1-5 μm in diameter. This lawn was composed of platy crystals (FIG. 6b). These macroporous coatings were less mechanically stable than coatings made in the inverted horizontal orientation and cells on these coatings were difficult to observe using an inverted microscope. Coatings like this were washed and harvested while wet for powder XRD analyses due to an increased mass compared with inverted coatings.

Figure 7:
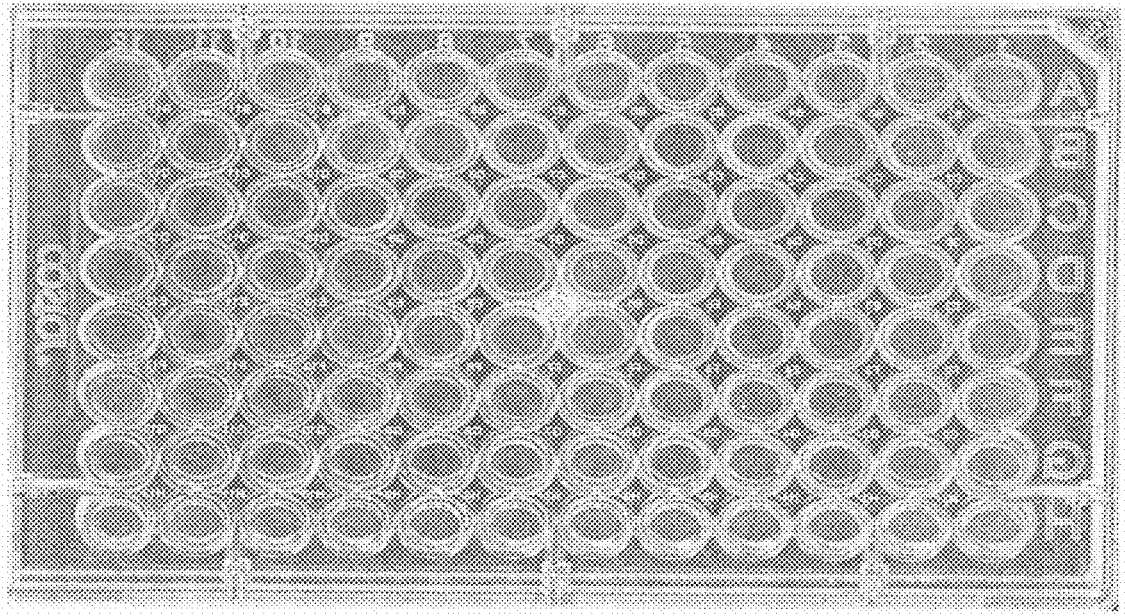
FIG. 7 shows the scanned image of a 96 well plate coated by the methods of the present invention.
Figure 8:
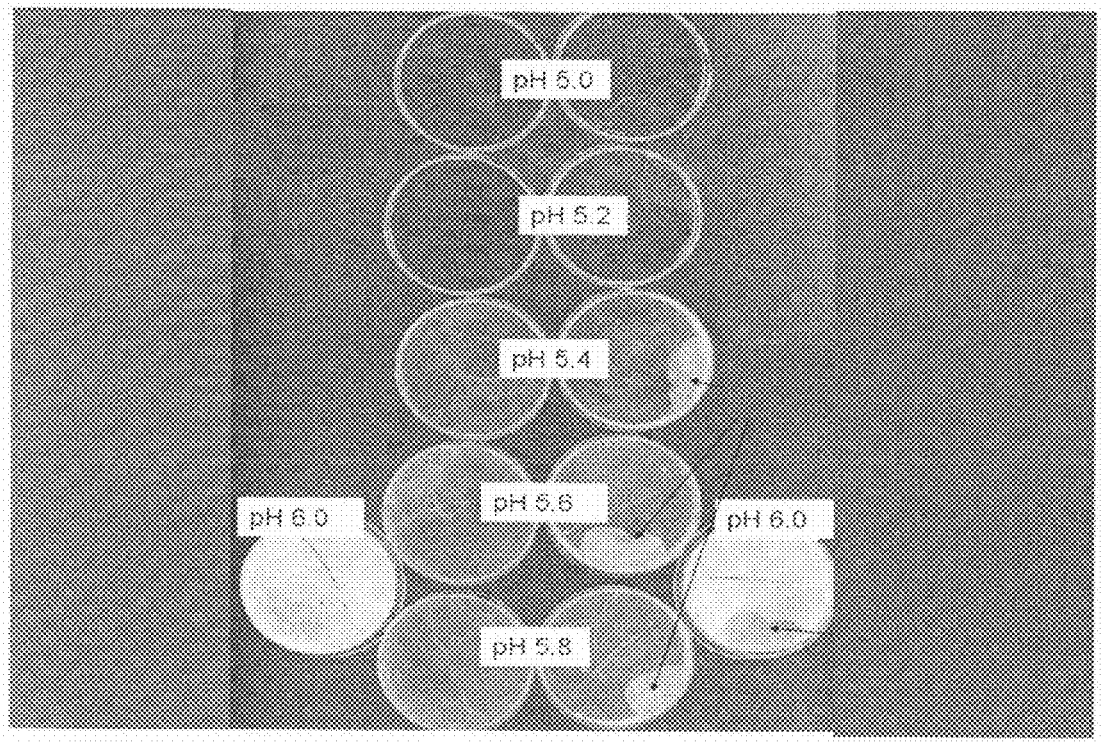
FIG. 8 shows the scanned image of Petri dishes coated by the methods of the present invention.

FIGS. 7 and 8 are scanned images of coatings on a microplate and Petri dishes, respectively. FIG. 7 shows the scanned image of a 96 well TCT PS plate incubated with SBF5X- at initial pH of pH 5.6 for 18 hours at 40° C. The microplate in FIG. 7 appears only slightly translucent when dry and coatings are uniform from well to well. FIG. 8 shows the scanned image of 60 mm Petri dishes incubated with SBF5X- with various starting pH levels for 18 hours at 40° C. The coatings in the dishes in FIG. 8, which were incubated upright, were much more opaque and lacked homogeneity. FIG. 8 shows a set of dishes incubated with various starting pH levels. Crystal violet lactone dye (CVL) is a leuco dye that reacts with weak acid and has been used in this study to identify calcium orthophosphates with acidic surface functionalities. A lack of crystal formation on the surface of the dishes was observed at pH 5-5.2 (i.e., no blue staining by CVL and the dishes appeared clear). Conversely, highly opaque coatings (amorphous, poorly adhered coating) were observed on the dishes with a starting pH of 6.0 (i.e., no blue staining by CVL). Only the dishes with a starting pH between 5.4-5.8 had translucent, well-adhered crystalline coatings, which stained positive (blue) with CVL in xylene. Coatings on microplates prepared at similar starting pH ranges also reacted positively with CVL.

Figure 2A:
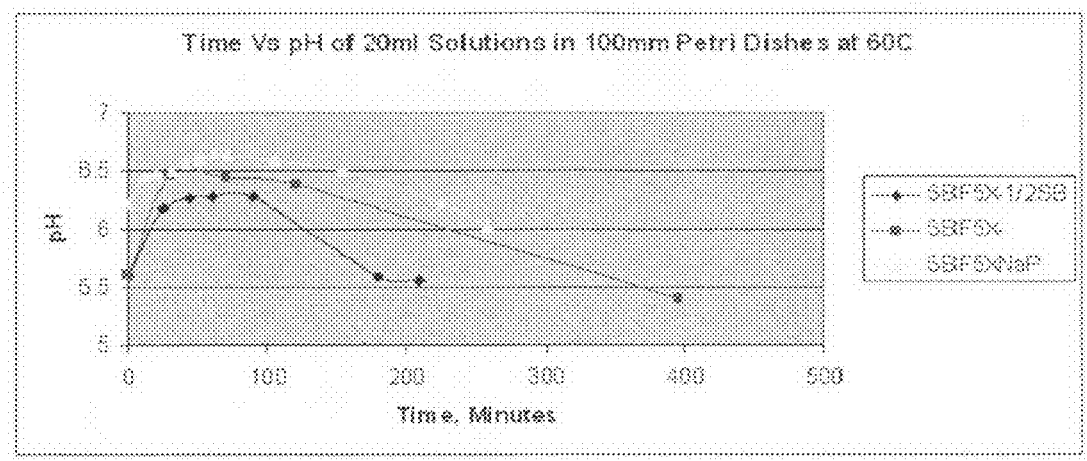
FIG. 2a shows the pH kinetics of three different solutions containing precursor components (SBF5X-, SBF5X-1/2SB, and SBF5XNaP) in Petri dishes during incubation.

FIG. 2a shows the pH kinetics of three solutions in the Petri dishes; SBF5X-, SBF5X-1/2SB, and SBF5XNaP. In this experiment, 20 ml of solution was added to 100 mm TCT dishes which were incubated at 60° C. Solutions became cloudy during the crystal nucleation phase. The dish with SBF5X-1/2SB reached a lower maximum pH compared with the other two. All three solutions demonstrated an initial rise in pH and subsequent fall, and all 3 resulted in HA coatings on dishes.

Figure 2B:
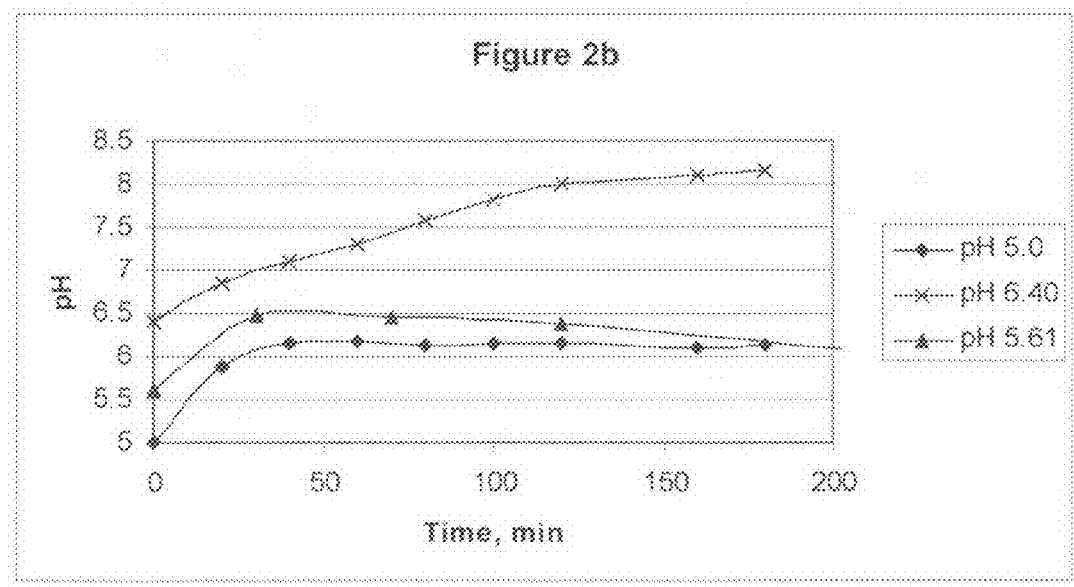
FIG. 2b shows a graph of time vs. pH for a solution containing a plurality of precursor components (SBF5X-) with different starting pH levels during incubation.

FIG. 2b shows a graph of time vs. pH for SBF5X- solutions with different starting pH levels (20 ml of solution was added to 100 mm TCT dishes). The Petri dishes were covered and incubated (not inverted) at 60° C. It is believed that the initial rise in pH in FIGS. 2a and 2b is due to release of $CO_2$ gas from solution when bicarbonate is protonated to produce $H_2CO_3$, which ultimately produces $CO_2$ and water. This reaction rate was increased by increasing the temperature of solution during incubation. As the pH rises, salts become less soluble and precipitate out of solution. The pH of the solution that produced hydroxyapatite also decreased slightly over time, which is different from the solution pH that produced an amorphous precipitate where the pH steadily increased over time. Other factors discussed above for affecting the rate of heteronucleation to produce HA crystals include the charge of the substrate surface due to surface treatment (e.g., corona treatment) and the ability of $CO_2$ to escape when it is produced, which may depend upon the volume and thickness of mineral solution used to coat the substrate. All three solutions show an initial pH increase, but only SBF5X-, starting at pH 5.6 showed a significant crystal growth phase (i.e., measurable decrease of pH over time).

Example 6

Low crystalline HA

Figure 9A:
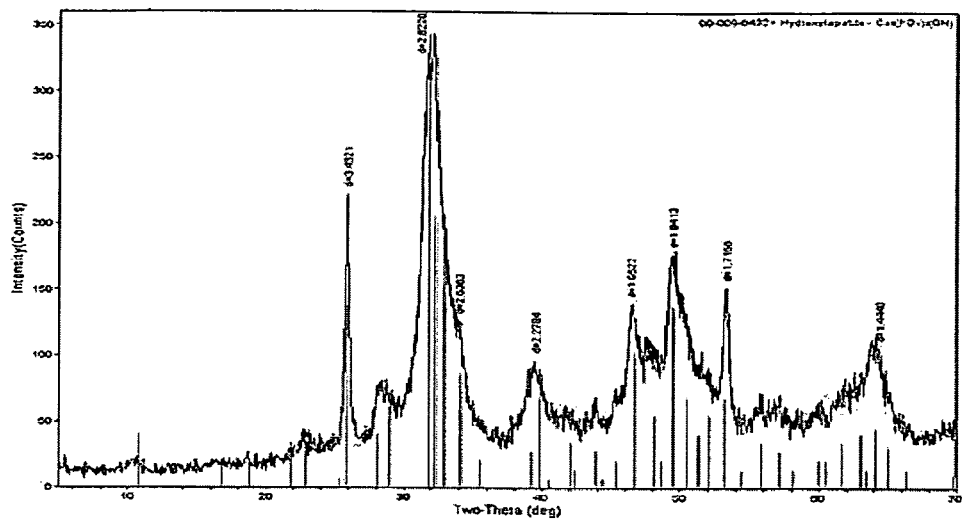
FIGS. 9a, 9b, and 9c show X-ray Diffraction patterns of coatings produced by the methods of the present invention.
Figure 9B:
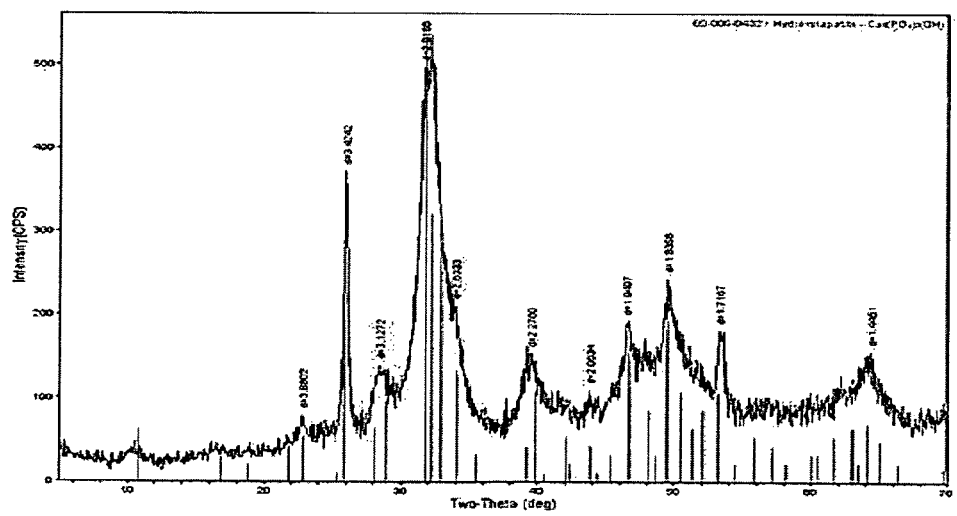
Figure 9C:
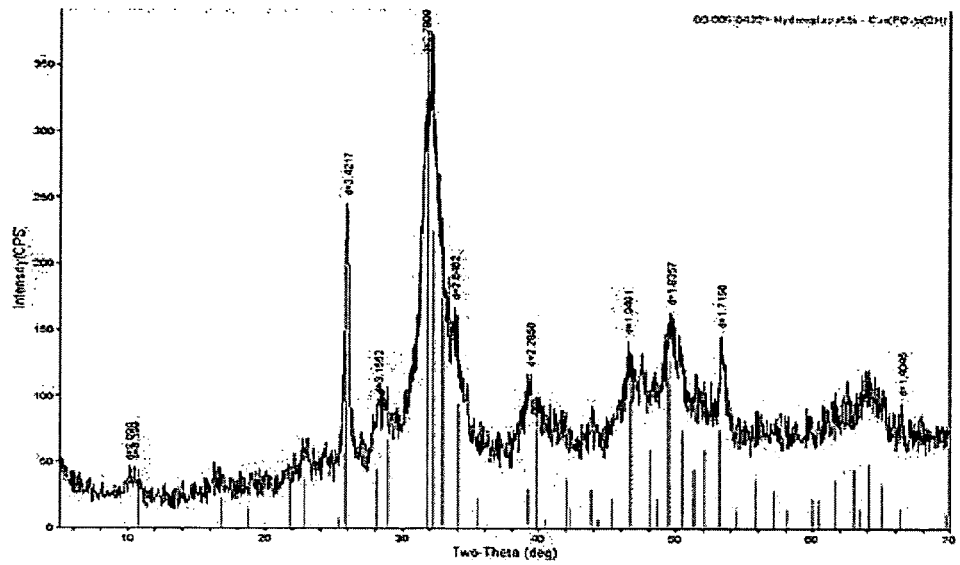

FIG. 9 shows powder XRD patterns of coatings scraped from Petri dishes incubated with pH 5.6 SBF5X- at 18 hours at 40° C. (FIG. 9a) and 4 hours at 60° C. (FIG. 9b). FIG. 9c shows an XRD pattern of coatings from a dish incubated with SBF5X-1/2SB incubated 4/60. Powder XRD patterns of coatings scraped from upright Petri dishes incubated for 18/40 and 4/60 exhibited a low crystalline hydroxyapatite pattern for the initial pH of 5.6 (FIGS. 9a and 9b), as demonstrated by broad peaks in the XRD pattern. This is considered to be a bone-like quality for crystalline materials. At the initial pH of 6-6.5, an amorphous precipitate formed and, as shown in FIG. 8, at lower pH no coating is formed. The same single phase coating XRD pattern was observed in the less homogeneous SBF5X-1/2SB coating (FIG. 9c). Therefore, this crystalline phase is the same as the thicker coatings.

Example 7

Magnesium Substitution for Calcium

This experiment shows that modified hydroxyapatite may be prepared by substituting a portion of calcium ions present in hydroxyapatite with magnesium ions. Induction coupled mass spectroscopy (ICP) was used to analyze coatings on the surface of the wells of 96 well TCT PS microplates incubated for 4 hours at 60° C. with SBF5X-. Coatings from several wells were dissolved in 1 M HCl and combined prior to analysis and data showed the Ca/P ratio was 1.44. The Ca/P ratio of hydroxyapatite (Aldrich cat#574791, 99.9%) was determined, and the ratio is 1.66. Previous analyses of similar coatings in single wells were dissolved by acid using ICP-MS, which indicated that coated wells consistently contained 0.5 ppm more magnesium ion compared with uncoated wells. The reduced value of the Ca/P ratio of the formed HA coating in addition to detection of magnesium ion in these coatings indicates that Ca ions were substituted with magnesium during crystalline formation. Thus, this procedure provides a method for producing magnesium modified hydroxyapatite.

Example 8

Carbonate Substitution

Figure 10:
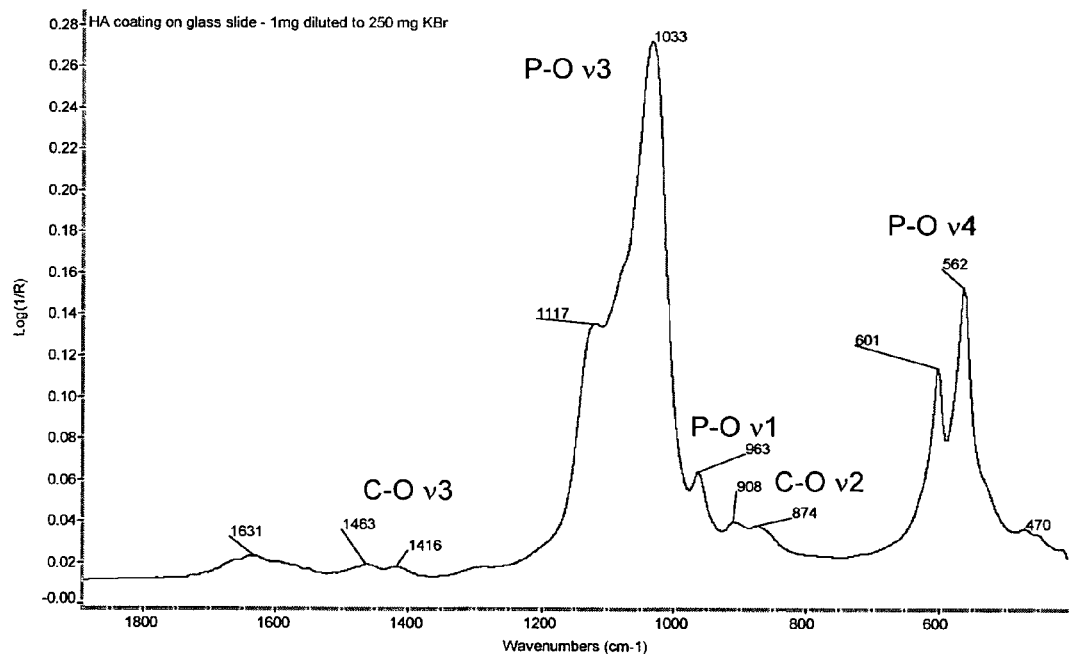
FIG. 10 shows DRIFTS FTIR results of a coating from a glass slide produced by the methods of the present invention.

This experiment shows that modified hydroxyapatite may be prepared by incorporating carbonate ions into hydroxyapatite. The mineralization solution SBF5X- was pre-incubated in a Petri dish prior to transfer of the solution to a vertical slide holder. A glass slide was then immersed in the slide holder and incubated for 18 hrs at 40° C. DRIFTS FTIR data of material scraped from the glass slide showed two C-O peaks, which indicates the presence of carbonate groups in the crystal structure (FIG. 10).

Example 9

Lung Cell Culturing and Evaluation

Figure 11A:
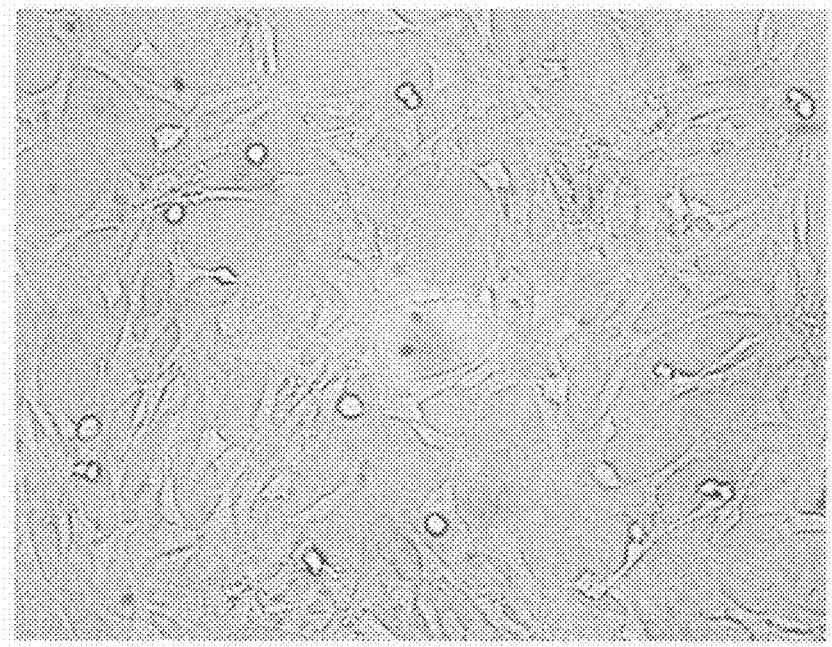
FIGS. 11a and 11b are optical micrographs of MRC5 cells on a 96 well microplates coated by the methods of the present invention.
Figure 11B:
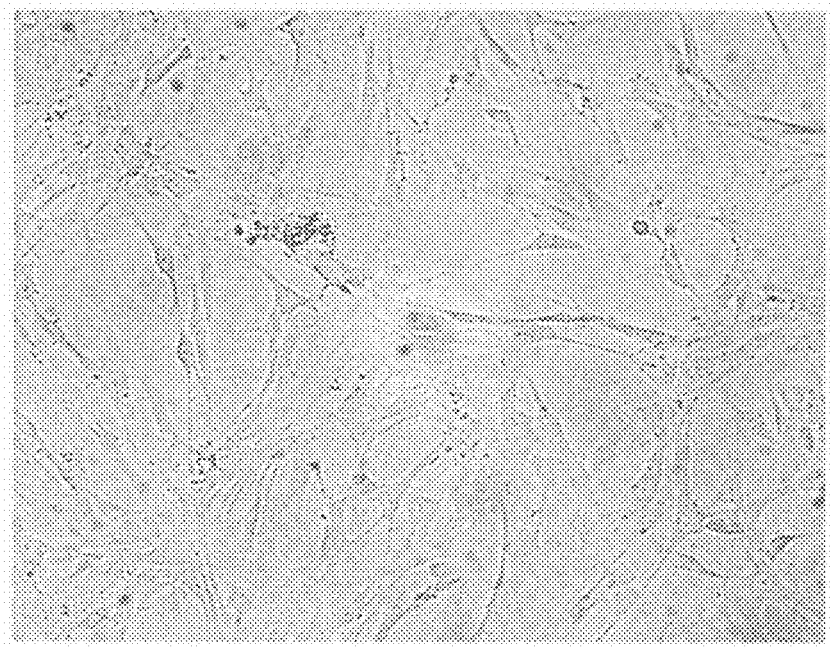
Figure 12:
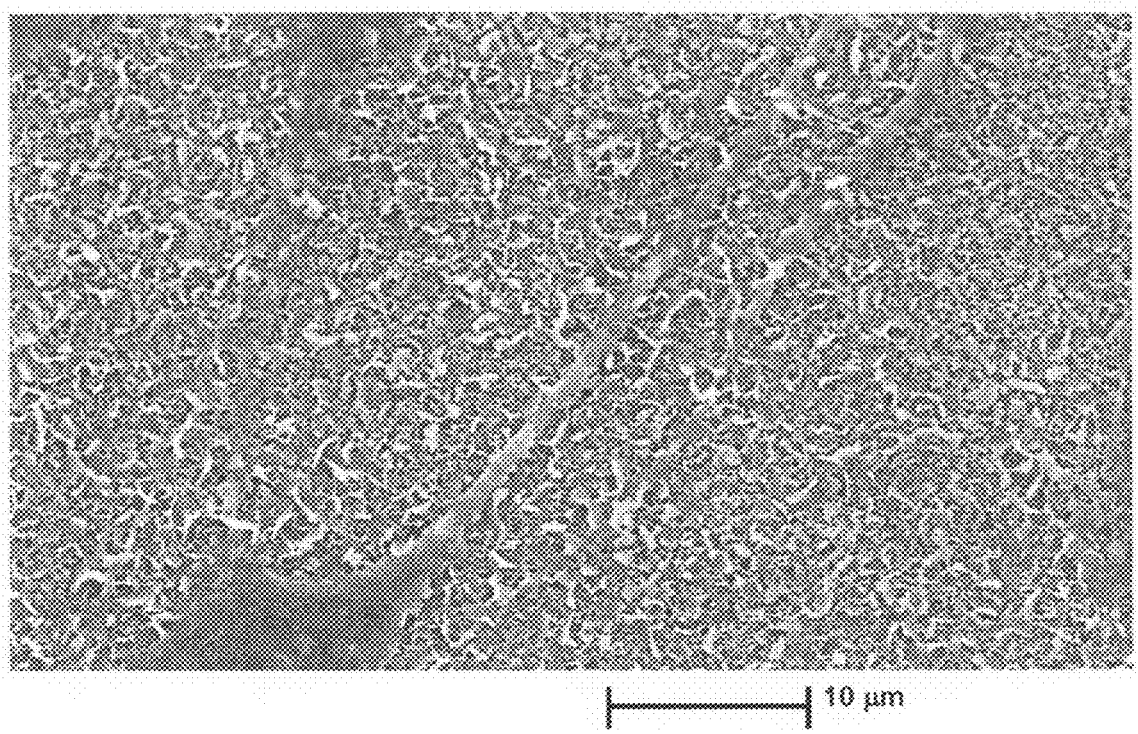
FIG. 12 shows an SEM micrograph of an MRC5 cell (human lung fibroblast) on a 96 well microplate coated by the methods of the present invention.

Two 96-well microplates (TCT PS with SBF5X- incubated at 18 hrs/40° C. or 4 hrs/60° C.) were plated with 5,000 cells per 100 µl per well (50,000 cells/ml). The cells were in Eagles Minimal Essential Medium with 10% FBS and penn/strep. The cells were incubated at 37° C. for 3 days and then observed by optical microscope and SEM. Cells are clearly visible as observed by inverted optical microscopy on 18/40 plates (FIG. 11a) and on 4/60 plates (FIG. 11b). A slight wormy texture was observed at 400 X (FIG. 11a), which may be attributed to the coating. FIG. 12 shows an SEM of an MRC5 cell on an 18/40 surface.

Example 10

Bone Cell Culturing and Evaluation

A 96 well plate (CNG with SBF5XNaP incubated at 18 hrs/40° C.) was used in this experiment and is referred to herein as the "the HA surface." The HA surface was tested in cell culture using a rat osteoclast (OC) precursor cell culture kit (OSC25 B-Bridge Intl.). This plate was tested in parallel with a coated 16 well slide Becton Dickinson Osteologic™ 354608) (the Becton surface), which is a quartz slide coated with a sintered film of sol gel composed of calcium nitrate and ammonium phosphate with an assembly for creating the 16 wells. Cells were thawed and washed according to kit directions, then seeded at 50,000 cells/100 µl/well using provided culture medium on the HA surface and the Becton surface. The coated HA surface and Becton surface were incubated at 37° C. for 9 days in a 5% $CO_2$ incubator with fresh media added on days 3 and 6.

Precursor cells adhered to both surfaces soon after plating (no image provided). Precursor cells were small (<20 µm) and round. Cells with OC-like morphology (>100 µm and multinuclear) were seen by day 9 in culture on both substrates. On day 9, cells in some wells were fixed and stained using a tartrate resistant acid phosphatase (TRAP) stain kit (AK04 B-Bridge Intl.). This stain is specific for OC cells and is used in combination with cell morphology and pit formation to identify osteoclast cells. Cells in the remaining wells were removed with 10% bleach (sodium hypochlorite) for 5 minutes and coatings were observed by SEM and optical microscopy for pits.

Osteoclast cells formed (i.e., differentiated) from precursor cells on both the HA surface and the Becton surface. Individual cells (as indicated by the arrows) were more clearly visualized on the HA surface (FIG. 13a) than the Becton surface (FIG. 13b). The better resolution in FIG. 13a provides easier cell counting and evaluation compared to FIG. 13b. Referring to FIG. 14, resorption pits formed on both surfaces. The pits are the dark images in FIGS. 14a and 14b. The resorption pits present on the HA surface (FIG. 14a) were more defined by both SEM and optical microscopy (not shown) compared to the Becton surface (FIG. 14b). The use of image analysis of micrographs for measuring the percent of pits is common, and would be more easily accomplished with more precision using the HA surface compared to the Becton surface.

Various modifications and variations can be made to the materials, methods, and articles described herein. Other aspects of the materials, methods, and articles described herein will be apparent from consideration of the specification and practice of the materials, methods, and articles disclosed herein. It is intended that the specification and examples be considered as exemplary.

What is claimed is:

1. A method for coating a multi-well substrate having a plurality of wells with crystals comprising calcium phosphate, comprising:
   (a) introducing into the wells of the substrate solutions comprising a plurality of precursor components of the crystals comprising calcium phosphate in concentrations for producing the crystals wherein each of the solutions has initial pH from 5 to less than 7.0;
   (b) inverting the substrate, wherein the solutions remain at the bottom of the wells of the inverted substrate due to the surface tensions of the solutions in the wells of the inverted substrate; and
   (c) incubating the inverted substrate for a time at an appropriate temperature so that the crystals comprising calcium phosphate are produced and coated on the surface of at least one well of the wells of the substrate and a gas generated by the reactions of the plurality of precursor components in the solutions during the incubation is released out from the wells.

2. The method of claim 1, wherein the substrate comprises a polymer selected from the group consisting of polystyrene, polypropylene, polycarbonate, and polyester.

3. The method of claim 1, wherein the substrate comprises an inorganic material.

4. The method of claim 3, wherein the inorganic material comprises glass, quartz, ceramic, silica, a metal oxide, or any combination thereof.

5. The method of claim 1, wherein prior to step (a), the substrate has been modified to increase the amount of surface oxygen on the surface of the substrate.

6. The method of claim 1, wherein the substrate comprises polystyrene.

7. The method of claim 1, wherein the introducing step comprises partially filling the wells of the substrate with the solutions.

8. The method of claim 1, wherein the substrate comprises a glass slide, wherein the wells are formed by a gasket which is adhered to the slide to provide temporary wells.

9. The method of claim 1, wherein the precursor components comprise calcium chloride, magnesium chloride, sodium bicarbonate, potassium hydrogen phosphate, sodium phosphate, and sodium chloride.

10. The method of claim 9, wherein the solutions in step (a) further comprise one or more bioactive molecules.

11. The method of claim 10, wherein the one or more bioactive molecules comprise collagen.

12. The method of claim 1, wherein the crystals comprise hydroxyapatite or substituted hydroxyapatite.

13. The method of claim 1, wherein the solutions of precursor components comprises Simulated Body Fluid (SBF) wherein the SBF is synthetic and wherein the synthetic SBF is described as synthetic NXSBF, where N is greater than 0, and where NX is a multiplier with respect to the concentration of the synthetic SBF.

14. The method of claim 1, wherein the initial pH from 5 to less than 7.0 is pH from 5 to 6.5.

15. The method of claim 1, wherein the method comprises optionally inserting a gas-permeable membrane into the wells of the substrate to prevent leakage of the solutions from the wells upon said inverting the substrate prior to the incubation step.

16. The method of claim 1, wherein the incubation step is performed at a temperature up to 90 ° C. for up to 72 hours.

17. The method of claim 1, wherein steps (a)-(c) are performed multiple times sequentially.

18. The method of claim 1, wherein after the incubation step, the coated surface of the at least one well of the wells of the substrate is washed with water, dried, and sterilized.

19. The method of claim 1, wherein further comprising after step (c), applying one or more bioactive molecules to the coated surface of the at least one well of the wells of the substrate.

* * * * *